(12) United States Patent
Cianfrani et al.

(10) Patent No.: US 10,456,181 B2
(45) Date of Patent: Oct. 29, 2019

(54) SPINAL PLATE ASSEMBLY HAVING LOCKING MECHANISM

(71) Applicant: GLOBUS MEDICAL, INC., Audubon, PA (US)

(72) Inventors: Jason Cianfrani, East Norriton, PA (US); Ross Morris, Norristown, PA (US)

(73) Assignee: Globus Medical, Inc., Audubon, PA (US)

( * ) Notice: Subject to any disclaimer, the term of this patent is extended or adjusted under 35 U.S.C. 154(b) by 494 days.

(21) Appl. No.: 14/993,369

(22) Filed: Jan. 12, 2016

(65) Prior Publication Data

US 2017/0196606 A1 Jul. 13, 2017

(51) Int. Cl.
*A61B 17/80* (2006.01)
*A61B 17/86* (2006.01)
*A61B 17/70* (2006.01)

(52) U.S. Cl.
CPC ...... *A61B 17/8605* (2013.01); *A61B 17/8042* (2013.01); *A61B 17/7059* (2013.01)

(58) Field of Classification Search
CPC ............ A61B 17/8605; A61B 17/8042; A61B 17/7059; A61B 17/8014; A61B 17/8033; A61B 17/8047; A61B 17/7061; A61B 17/8052; A61B 17/8615; A61B 2017/00862
USPC ...................................... 606/70–71, 280–299
See application file for complete search history.

(56) References Cited

U.S. PATENT DOCUMENTS

| | | | |
|---|---|---|---|
| 2005/0021032 A1* | 1/2005 | Koo | A61B 17/7059 606/295 |
| 2009/0054930 A1* | 2/2009 | Aflatoon | A61B 17/7059 606/246 |
| 2009/0131988 A1* | 5/2009 | Bush, Jr. | A61B 17/8042 606/280 |
| 2010/0016901 A1* | 1/2010 | Robinson | A61B 17/8042 606/289 |
| 2010/0241174 A1* | 9/2010 | Robinson | A61B 17/8042 606/289 |
| 2013/0030465 A1* | 1/2013 | Hess | A61B 17/7059 606/246 |
| 2013/0053887 A1* | 2/2013 | Predick | A61B 17/7059 606/246 |

* cited by examiner

*Primary Examiner* — Kevin T Truong
*Assistant Examiner* — Jessica Weiss

(57) ABSTRACT

A spinal plate assembly comprising a base plate defining an opening adjacent at least one aperture for receiving a bone screw which attaches to a spinal vertebrae. The aperture includes a seat and an annular groove having an end wall. The assembly comprises a locking mechanism having a split ring partially recessed within the annular groove and moveable between a locked condition partially blocking the aperture for retaining the screw in the seat and an unlocked condition radially deformable into the annular groove for permitting screw removal. The split ring has a proximal end and a distal end. The distal end is configured to engage the end wall of the annular groove. The locking mechanism comprises a rotating member retained within the opening of the base plate and having a notch configured to engage the proximal end of the ring to drive the ring toward the unlocked condition.

20 Claims, 23 Drawing Sheets

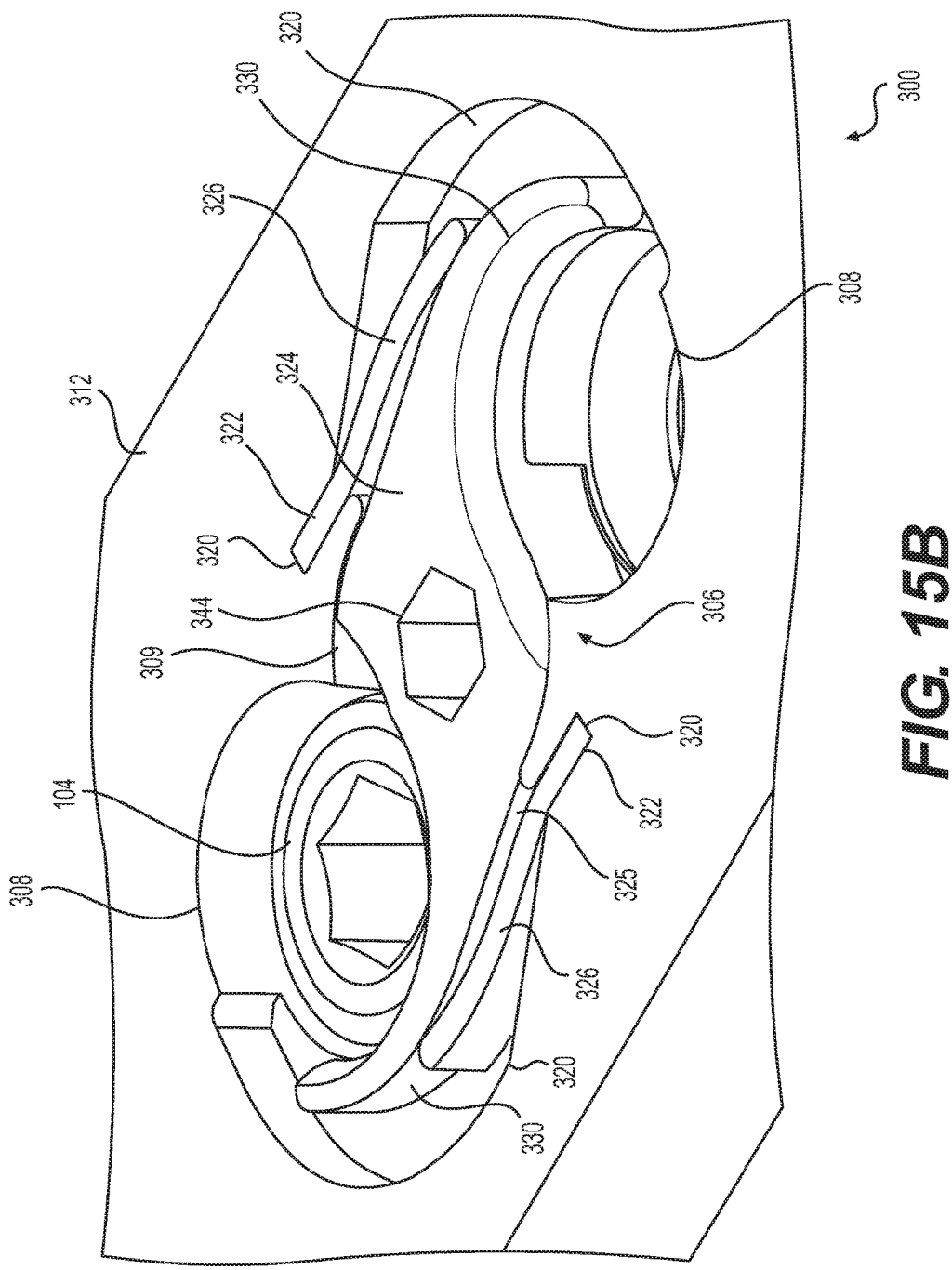

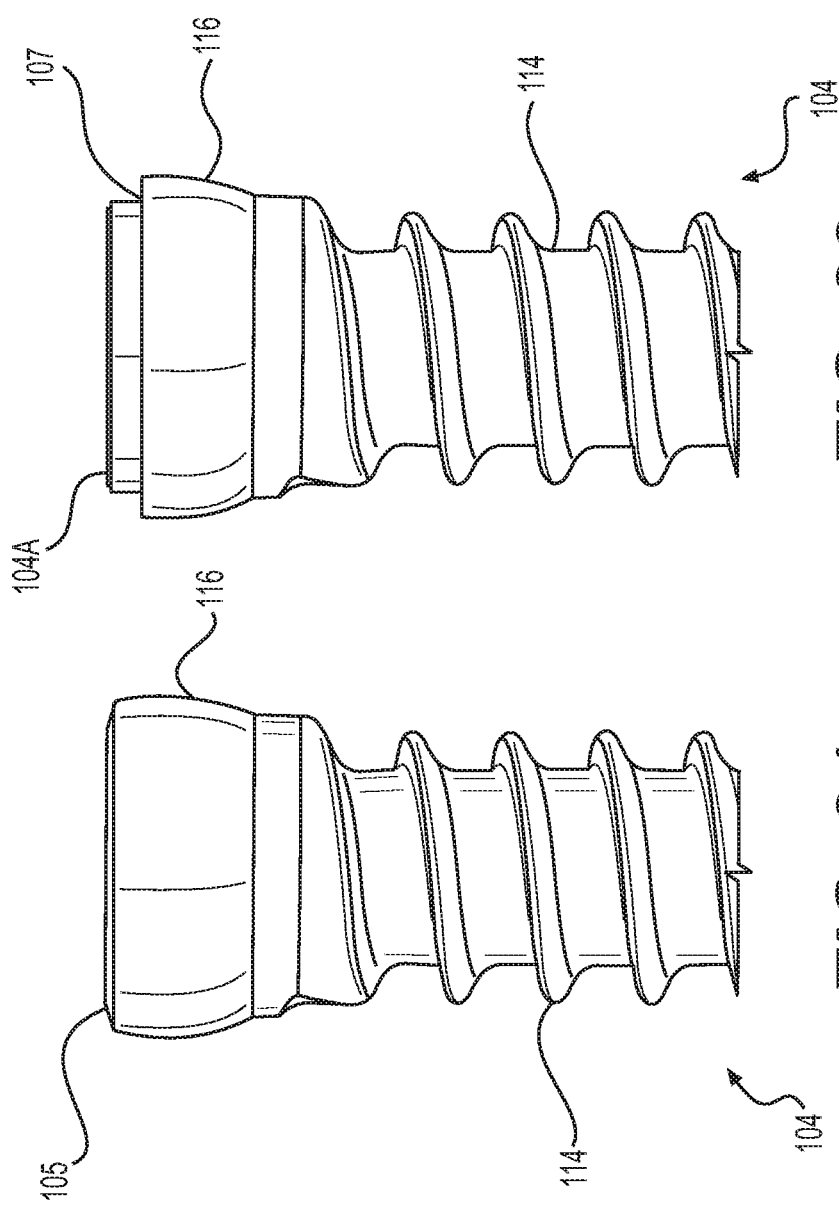

SPINAL PLATE ASSEMBLY HAVING LOCKING MECHANISM

FIELD OF THE INVENTION

The present invention relates generally to spinal plates used for fusing vertebrae in the treatment of spinal disorders, and more particularly to an improved locking mechanism within the plate assembly for securing bone screws in position after insertion and allowing for easy removal and readjustment.

BACKGROUND OF THE INVENTION

For over three decades plates have been used to increase stability of the spine following surgery to promote proper healing of injured or damaged vertebrae caused by disease, trauma, spinal defect, accident or the like. Conventional spinal plates are generally implanted during surgery by mounting to one or more vertebrae using bone screws. These plates often employ a locking mechanism to reduce the likelihood of screws disconnecting, reverse threading, backing out or otherwise pulling away from vertebrae in which they are mounted. Traditional locking mechanism employ securing caps, cover plates, bearings, screws with novel thread designs, and the like, in order to prevent the screws from disengaging the vertebrae. However, many of these locking mechanisms are ineffective, cumbersome, complicated and time consuming to apply, and unnecessarily expensive.

In addition, many of these locking mechanisms are unable to provide convenient manipulation and readjustment of the bone screws and plate during revision surgery. Those that do, require cumbersome instrumentation and complicated techniques to unlock and remove or readjust. This increases the patient's chances of being exposed to infection and, moreover, moves away from the industry's desire to decrease time spent in the operating room.

Therefore, there exists a need to provide a plate assembly having an improved locking mechanism that can cure some of the deficiencies in the prior art.

SUMMARY OF THE INVENTION

The present invention cures some of the deficiencies in the prior art by providing a spinal plate assembly having an improved locking mechanism for conveniently fixing screws in a locked position without the need for cumbersome hardware and complicated instrumentality. The improved locking mechanism of the present invention also enables a surgeon to quickly and easily unlock, remove and readjust the bone screw and plate after locking has taken place.

In an illustrative embodiment of the present invention, a spinal plate assembly comprises a base plate defining a substantially circular opening between a pair of apertures for coupling adjacent to a spinal vertebrae. The aperture includes a seat and an annular groove having an end wall. The assembly further comprises bone screws sized to be inserted through each aperture such that the bone screw sits within the seat of the aperture for engaging the spinal vertebrae. The assembly further comprises a locking mechanism having a split ring partially recessed within the annular groove of each aperture and moveable between a locked condition and an unlocked condition. Each split ring has a proximal end and a distal end. The distal ends are configured to engage the end walls of the respective annular grooves. The split rings are radially deformable within their respective annular grooves between the locked condition partially blocking the aperture for retaining the bone screws in the seat and the unlocked condition radially deformable into the annular groove for permitting the bone screws to be removed from the apertures. The locking mechanism further comprises a rotating member retained within the opening of the base plate having first and second diametrically opposed notches configured to engage the proximal ends of the split rings to simultaneously drive the split rings toward the unlocked condition. The rotating member includes a bore having a cross-section shaped to receive a conventional driving tool, thereby providing faster and easier removal of bone screws without the need for complicated instrumentation.

These advantages of the present invention will be apparent from the following disclosure and the appended claims.

BRIEF DESCRIPTION OF THE DRAWINGS

FIG. 15B is a perspective view of a spinal plate assembly having an integrated locking mechanism including a screw shown in an "as inserted" condition according to an alternate embodiment of the present invention.

FIG. 21 is a plan view of the bone screw in accordance with an illustrative embodiment of the present invention FIG. 22 is a plan view of the bone screw in accordance with an alternate embodiment of the present invention.

DETAILED DESCRIPTION

Rotating Member and Flexible Element and Annular Groove

Figure 1:
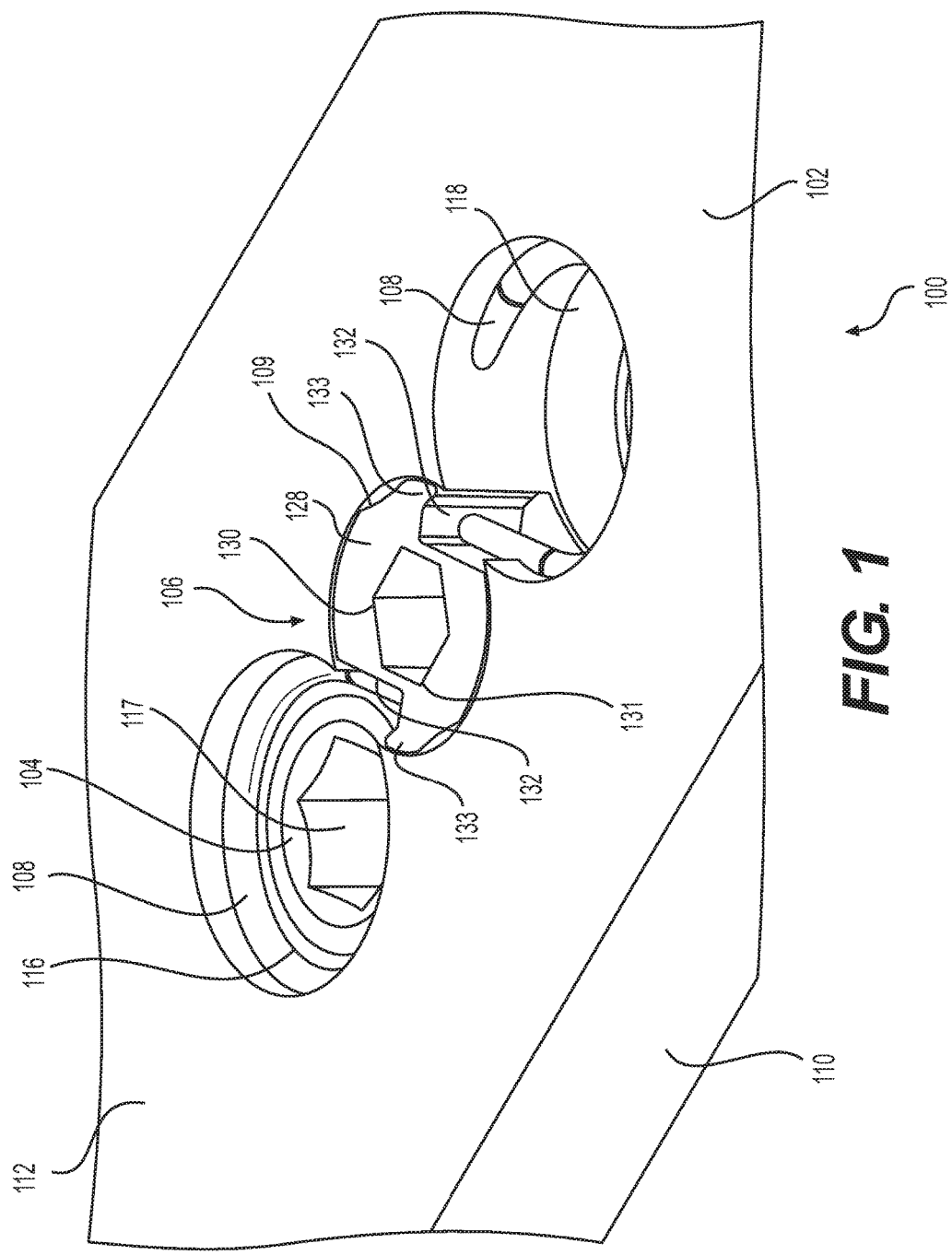
FIG. 1 is a perspective view of the spinal plate assembly having an integrated locking mechanism shown in a "locked" condition according to an illustrative embodiment of the present invention.
Figure 2:
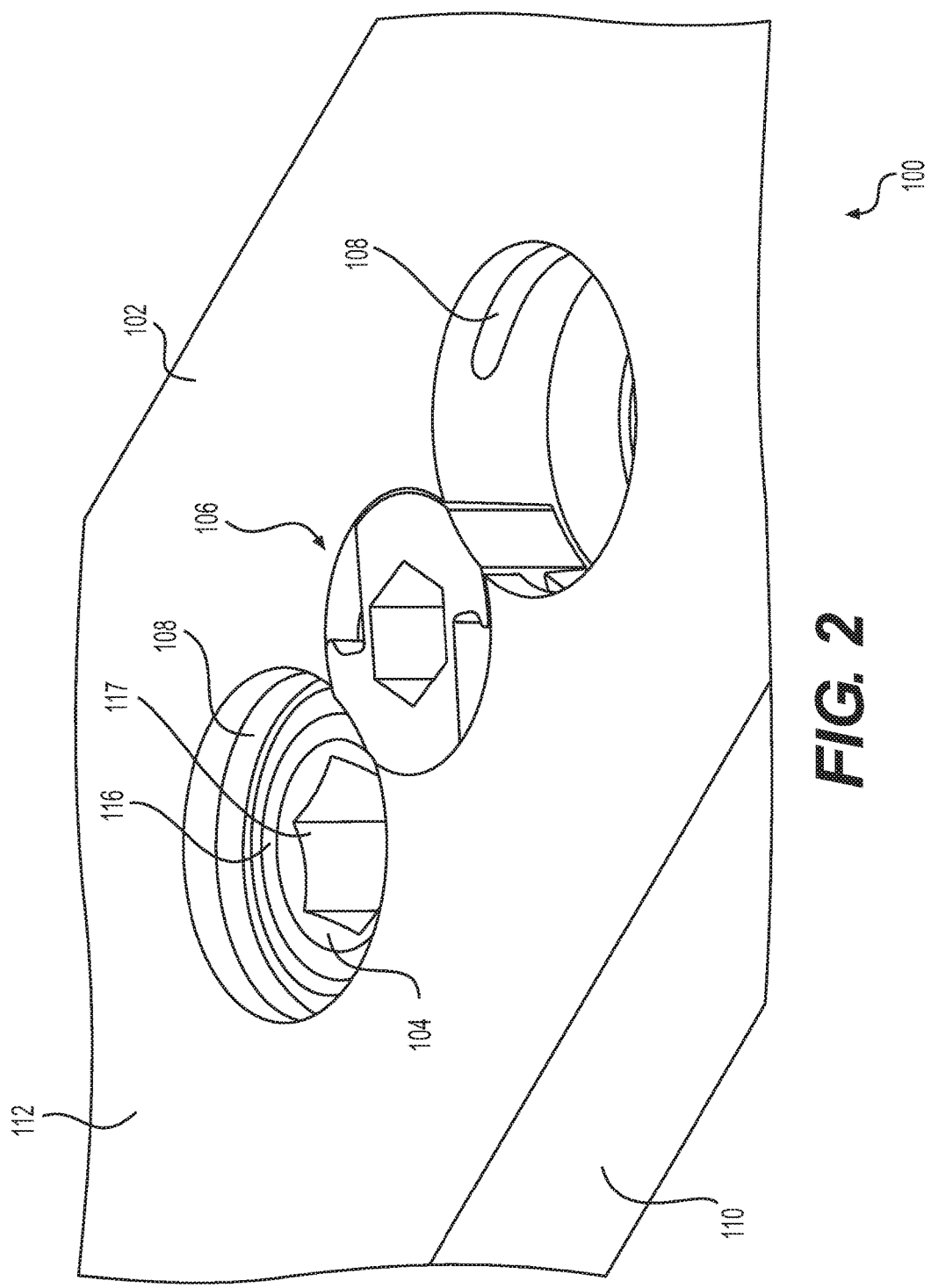
FIG. 2 is a perspective view of the spinal plate assembly of FIG. 1, wherein the locking mechanism is shown in an "unlocked" condition according to an illustrative embodiment of the present invention.

FIG. 1 is a perspective view of the spinal plate assembly 100 in a "locked" condition according to an illustrative embodiment of the present invention. FIG. 2 is a perspective view of the spinal plate assembly 100 in an "unlocked" condition according to an illustrative embodiment of the present invention. The spinal plate assembly 100 in these figures comprises: base plate 102, bone screw 104, locking mechanism 106, and aperture 108. The base plate 100 of the illustrative embodiment is preferably constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the elements of base plate 102 are made from a durable thermoplastic polymer, such as polyether ether ketone (PEEK).

It should be noted at this point of the disclosure that the locking mechanism of the present assembly 100 is adapted for use with plates and devices extending the spine and thoracic and lumbar regions, including but not limited to, cervical plates, thoracolumbar anterior and lateral plates.

In accordance with the illustrative embodiment, base plate 102 is an elongated structure having a lower surface 110 adapted to be placed against a plurality of vertebrae (not illustrated) and an opposite upper surface 112. In order to couple base plate 102 to vertebrae, base plate 102 has one or more apertures 108 therethrough for receiving one or more bone engaging fasteners, preferably bone screws 104. Bone screws 104 are implanted through apertures 108 to fix base plate 102 to adjacent vertebrae or bony element. Bone screws 104, shown in FIGS. 21-22, comprise an elongated threaded shank portion 114 that extends downwardly from an enlarged head portion 116 to fit inside aperture 108. The head portion 116 includes a tool recess 117, preferably a hexagonal or other non-circular recess, configured to receive a driving tool having similar profiled drive shaft (not shown). Preferably, shown in FIG. 21, shape of outside of head portion 116 of each bone screw 104 substantially corresponds to the shape of aperture 108, although this is not a requirement. Bone screw 104 includes a top 105, which may include a shoulder recess 107, shown in FIG. 22.

The base plate 102 includes at least one locking mechanisms 106 moveable between "locked" and "unlocked" conditions. In the "locked" condition, as shown in FIG. 1, bone screw head 116 is prevented from backing out of the aperture 108. In the "unlocked" condition, shown in FIG. 2, bone screw 104 is permitted to be removed from aperture 108.

Figure 3:
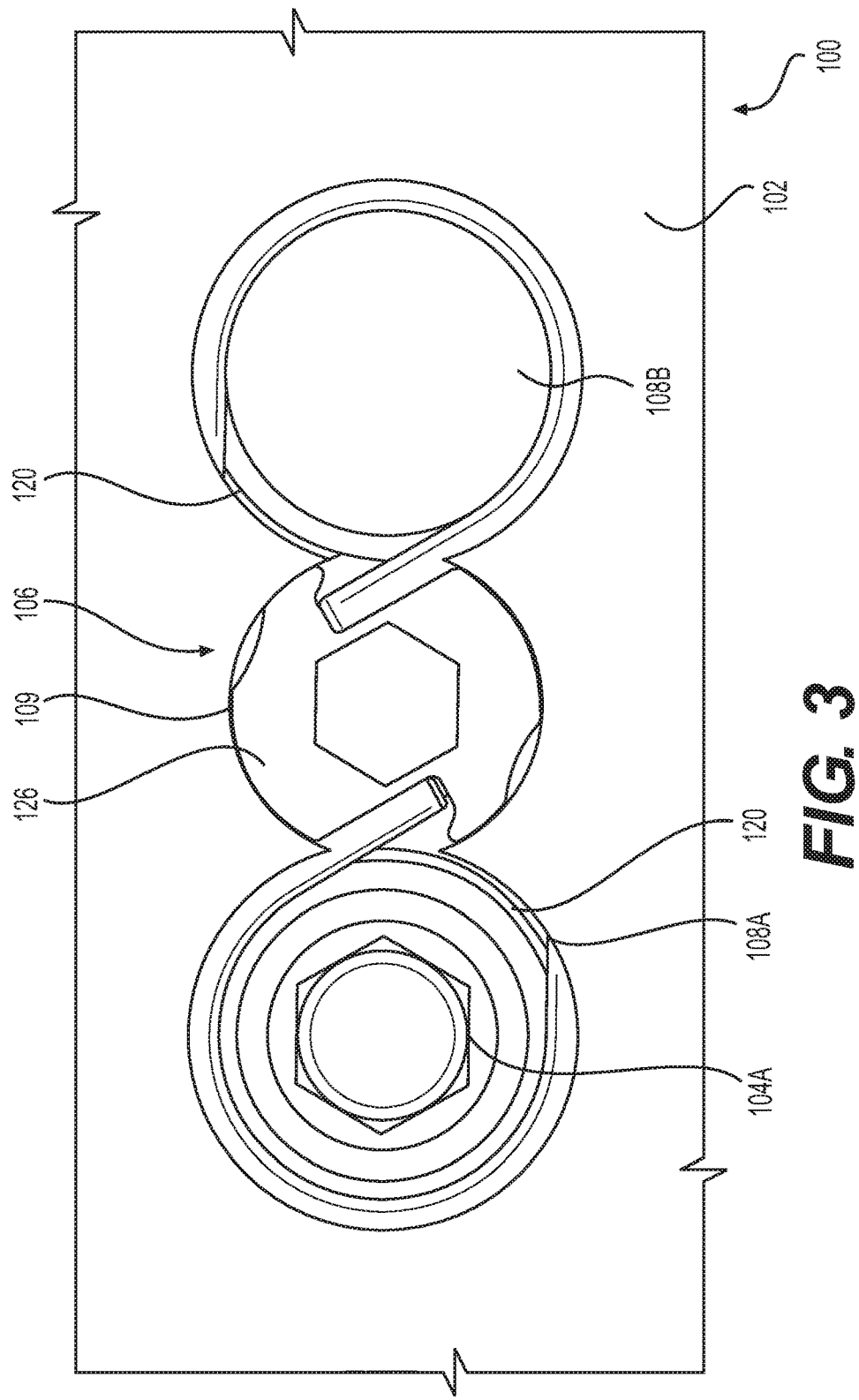
FIG. 3 is a top view of the spinal plate assembly of FIG. 1, depicting the elements that form the locking assembly in accordance with an illustrative embodiment of the present invention.

FIG. 3 is a top view of spinal plate assembly 100 and elements that form locking mechanism 106. Arranged within base plate 102 are apertures 108, each of which is sized and shaped to accommodate bone screw 104. Each aperture 108 includes a seat 118 and an annular groove 120 having an end wall 122. Specifically, the figure shows a first apertures 108A sized and shaped to receive a first screw 104A, while a second aperture 108B is sized and shaped to receive second screw 104B (not shown). Base plate includes at least one opening 109 adjacent the aperture 108 for receiving at least a portion of locking mechanism 106. Preferably, opening 109 is defined between two aligned apertures 108. It should be noted at this point of the disclosure that one or more apertures 108 is contemplated. In the case of one aperture (not sure) locking mechanism 108 controls one screw 104. In the case of three apertures (not shown) locking mechanism 108 controls three bone screws 104 disposed within three separate apertures 108 simultaneously. Apertures 108 are shown in more detail in the following figures, which will now be discussed. It should also be noted at this point of the disclosure that first aperture 108A and second aperture 108B are substantially similar, albeit rotated around the central axis thereof from one other, and that same reference numerals have been used to indicate same parts or elements throughout the various figures and specification. For the purpose of clarity, the following discussion will use the generic word "aperture 108," to refer to both first and second apertures 108A, 108B.

Figure 4:
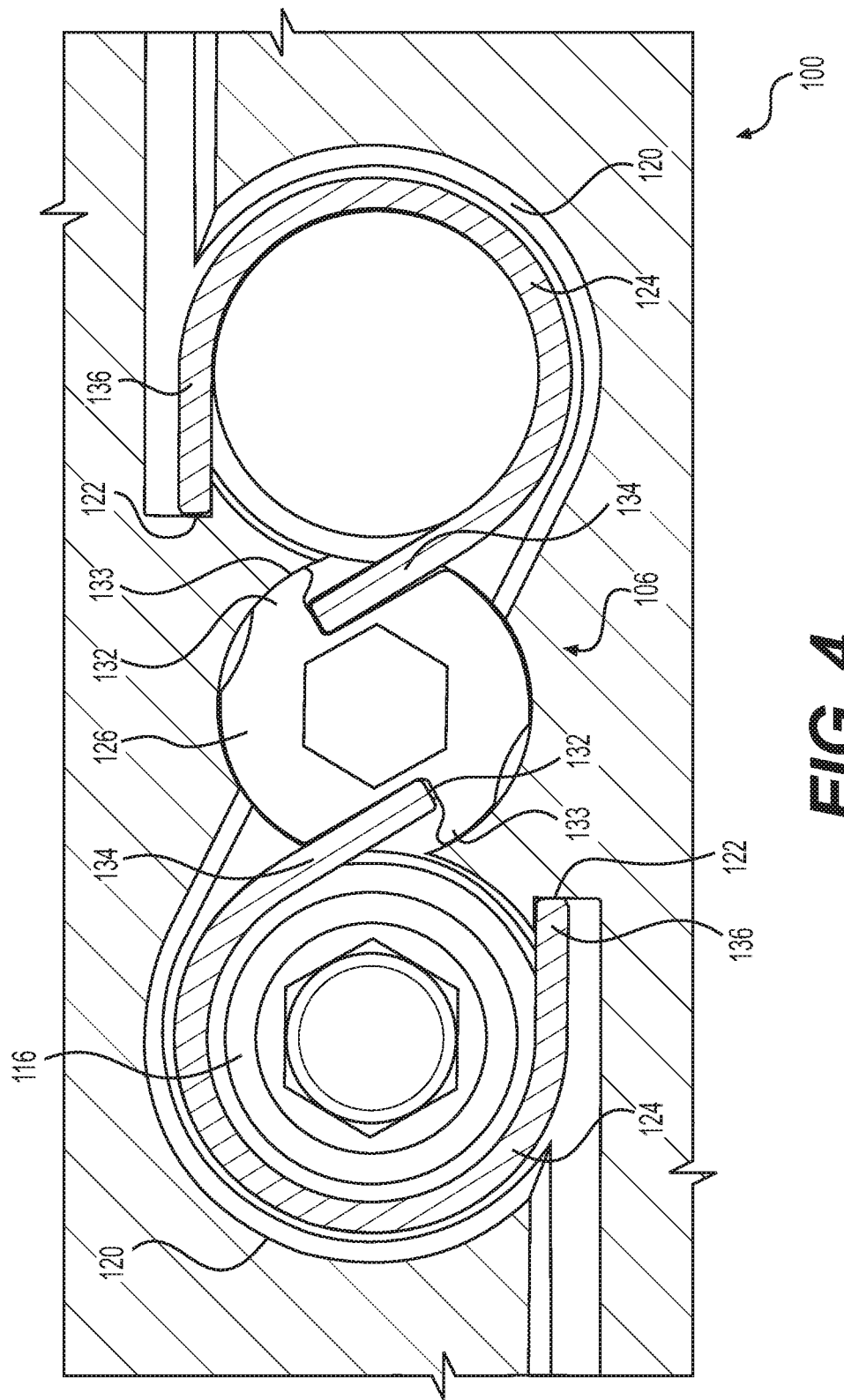
FIG. 4 is a top cross-sectional view of the spinal plate assembly of FIG. 1 in a "locked" condition in accordance with an illustrative embodiment of the present invention.

FIG. 4 is a cross-sectional view of the spinal plate assembly of FIG. 1 in the "locked" condition. In accordance with an illustrative embodiment, locking mechanism 106 comprises one or more flexible elements 124 and a moveable member 126 mounted therebetween. Preferably, moveable member 126 is a substantially cylindrical rotating member 126 arranged with a pair of generally diametrically opposed notches 132, including a first notch and a second notch that are sized and shaped to engage flexible elements 124 and create biasing force to radially deform flexible elements 124 within respective annular grooves 120. Preferably, opposed notches 132 are cutouts extending within edge of rotating member. Flexible element 124 is preferably a deformable split ring 124, at least partially retained within annular groove 120 of aperture 108. Split ring 124 includes a proximal end 134 and a distal end 136. Proximal end 134 is configured to engage notch 132 of rotating member 126, while distal end 136 is configured to engage end wall 122. Cutouts 132 include extensions 133 to retain proximal end 134 of flexible element 124 and provide extra leverage for unlocking.

Figure 5:
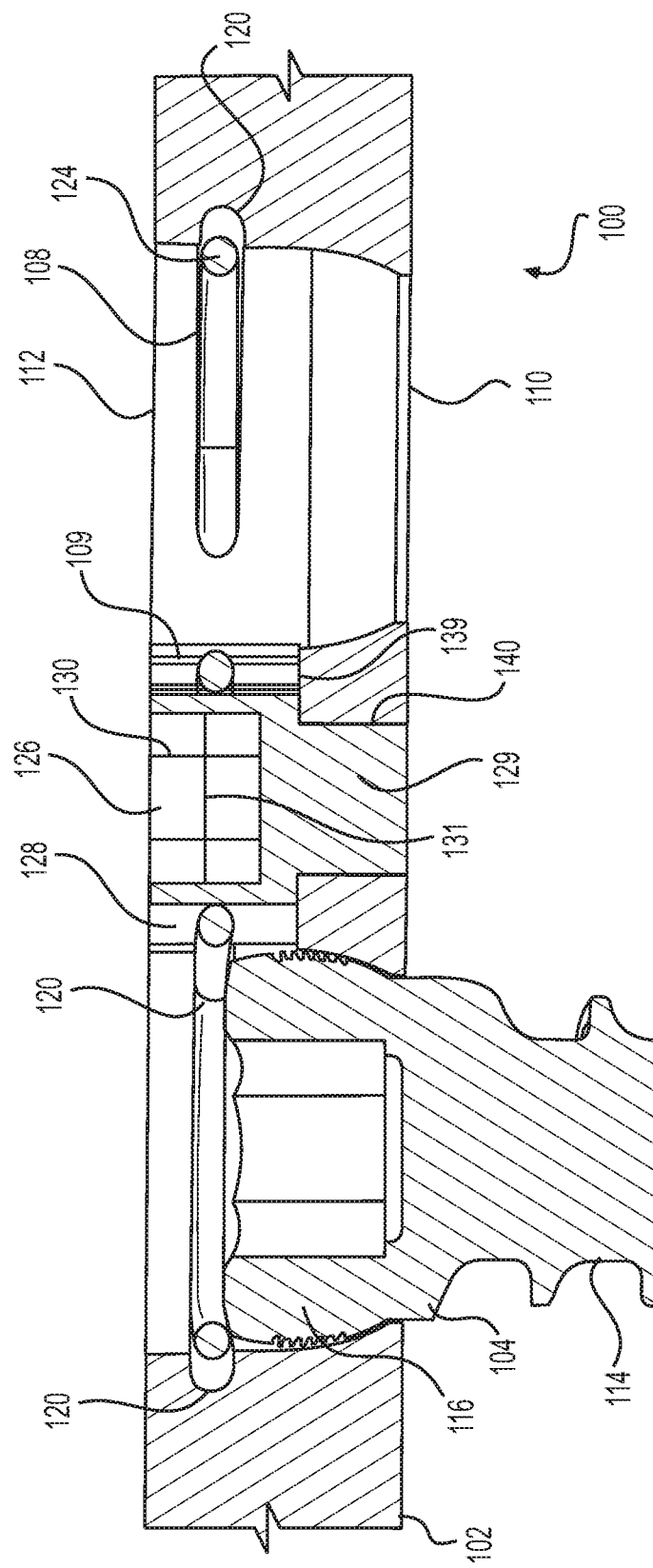
FIG. 5 is a side cross-sectional view of the spinal plate assembly of FIG. 1 in a "locked" condition in accordance with an illustrative embodiment of the present invention.

Split ring 124 is radially deformable into annular groove 120 as bone screw 104 is inserted into aperture 108, allowing bone screw head 116 to pass through and be seated in aperture 108. Once screw 104 is seated within aperture 108, as shown in FIG. 5, split ring 124 returns to "locked" condition partially blocking aperture 108 for retaining bone screw head 116. In particular, split ring 124 rests adjacent top 104A of bone screw 104. When bone screw 104 includes shoulder recess 104B, shown in FIG. 22, split ring 124 rests adjacent shoulder recess 104b, which reduces overall height of plate 102.

FIG. 5 is a cross-sectional view of the spinal plate assembly of FIG. 1 in the "locked" condition. Base plate 102 includes substantially cylindrical opening 109 arranged between apertures 108, which extends downwardly to a seat 139. Seat 139 of opening 109 includes a bore 140 extending axially therethrough. Rotating member 126 is generally cylindrical in shape and includes a substantially cylindrical head 128 having a substantially cylindrical pin 129 extending downwardly therefrom. Pin 129 is inserted within bore 140 of base plate 102 to pivotally connect rotating member 126 within opening 109 of base plate. Pin 129 may also include a threaded shaft (not shown) for securing the rotating member 126 within the opening 109. Head 128 of rotating member 126 is preferably mounted flush with upper surface 112 of base plate 102 so as to not intrude upon the body or working area of the base plate. Head 128 may also protrude (not shown) from the base plate 102 as desired.

Head 128 of rotating member 126 includes an engaging portion 130 for receiving a driver. Preferably, the engaging portion 130 is a recess having a cross-section 131 formed within head 128. Recess 130 allows a driving means, preferably a tool with a matching shaft (not shown), to rotate member 126 clockwise about pin 129 within opening 109. Tool as described in the illustrative embodiment has a hexagonal shaft for mating with a hexagonal recess 130 of head 128, but any other matching slotted, flat, triangle, square, star, rectangular, pentagonal, octagon, n-lobular, hexalobular, stardrive, Torx®, trilobular or other keyed shape is possible.

Figure 6:
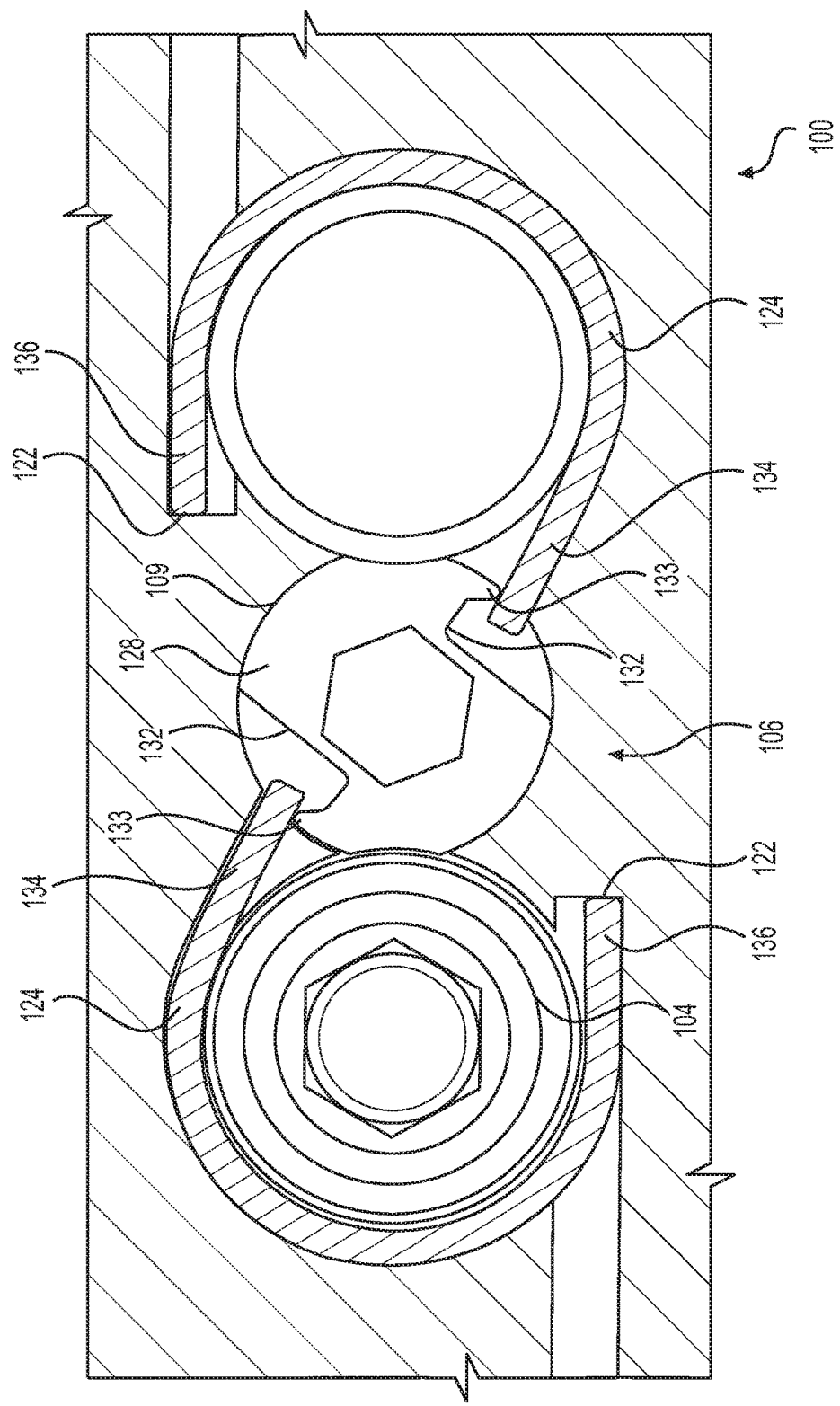
FIG. 6 is a top cross-sectional view of the spinal plate assembly of FIG. 2 in an "unlocked" condition in accordance with an illustrative embodiment of the present invention.
Figure 7:
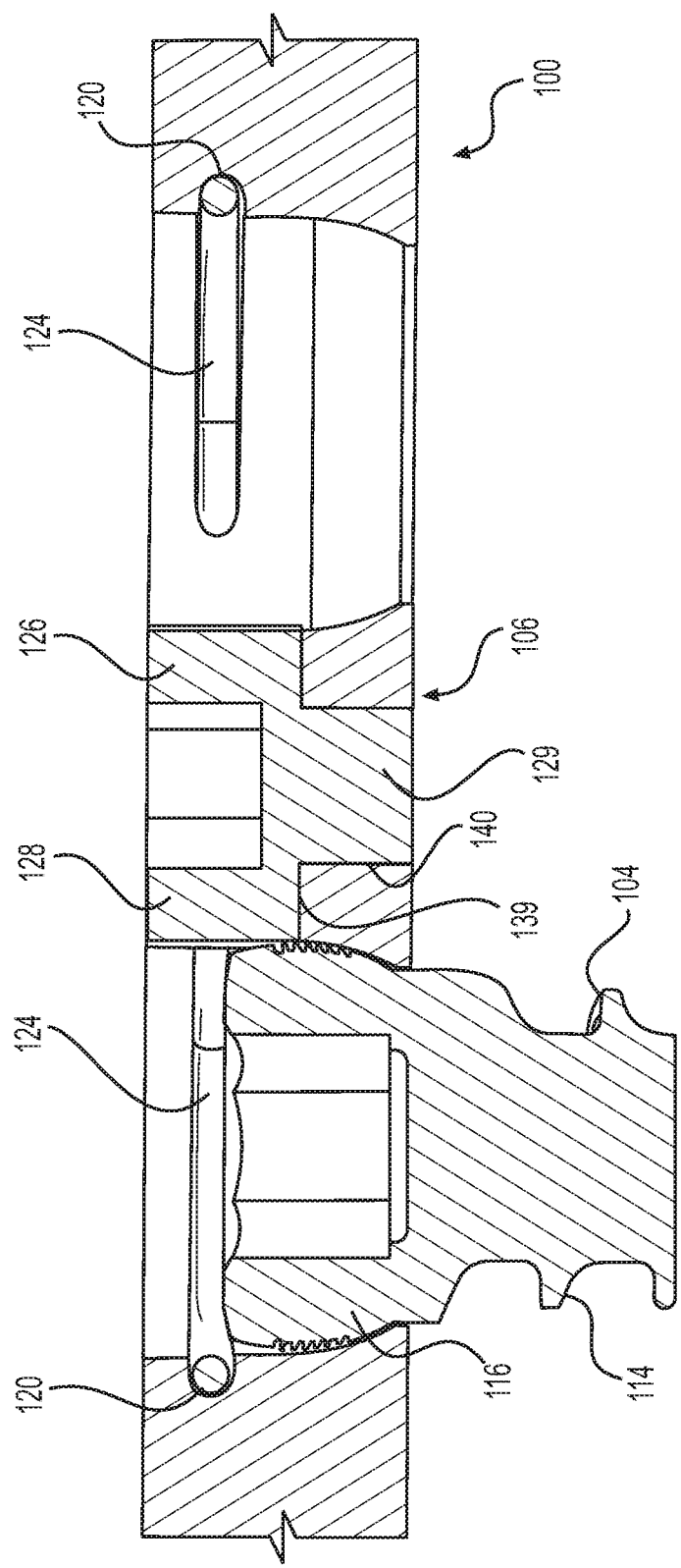
FIG. 7 is a side cross-sectional view of the spinal plate assembly of FIG. 2 in an "unlocked" condition in accordance with an illustrative embodiment of the present invention.

FIGS. 6 and 7 illustrate the spinal plate assembly of FIG. 2 in the "unlocked" condition to remove bone screw 104 from aperture 108. Rotating member 126 is rotated clockwise by driving means from "locked" to "unlocked" condition. As rotating member 126 is driven clockwise, notch 132 of rotating member 126 engages proximal end 136 of split ring 124 to force distal end of split ring 124 to engage end wall 122 and radially deform into annular groove 120. Using driving tool (not shown), bone screw is then removed from aperture 108.

In accordance with the illustrative embodiment, rotating member 126 is configured to engage proximal ends 134 of first and second split rings 124 so as to drive both rings 124 to the "unlocked" condition simultaneously.

Rotating Member Containing Flexible Element

Figure 8:
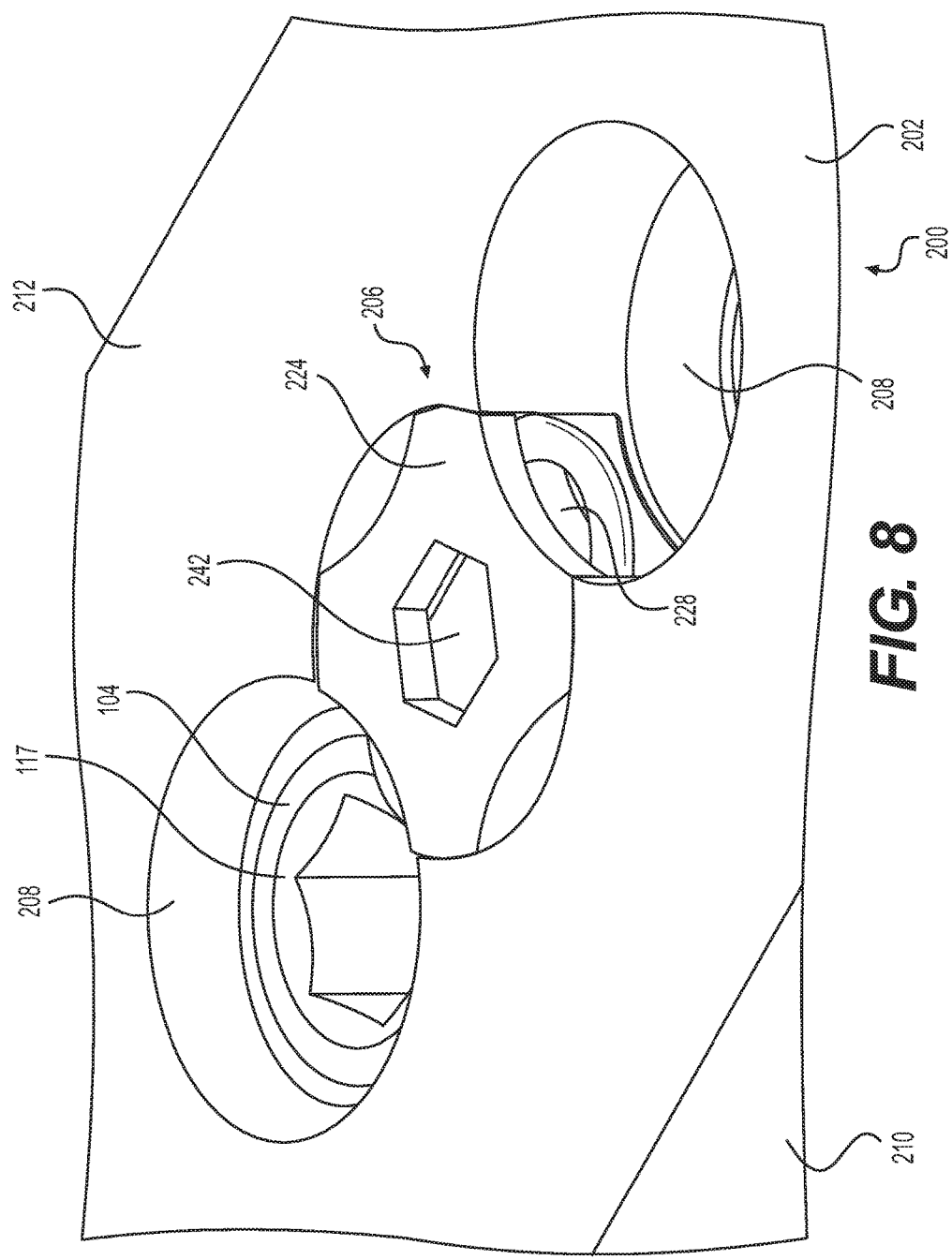
FIG. 8 is a perspective view of a spinal plate assembly having an integrated locking mechanism shown in a "locked" condition according to an alternate embodiment of the present invention.
Figure 9:
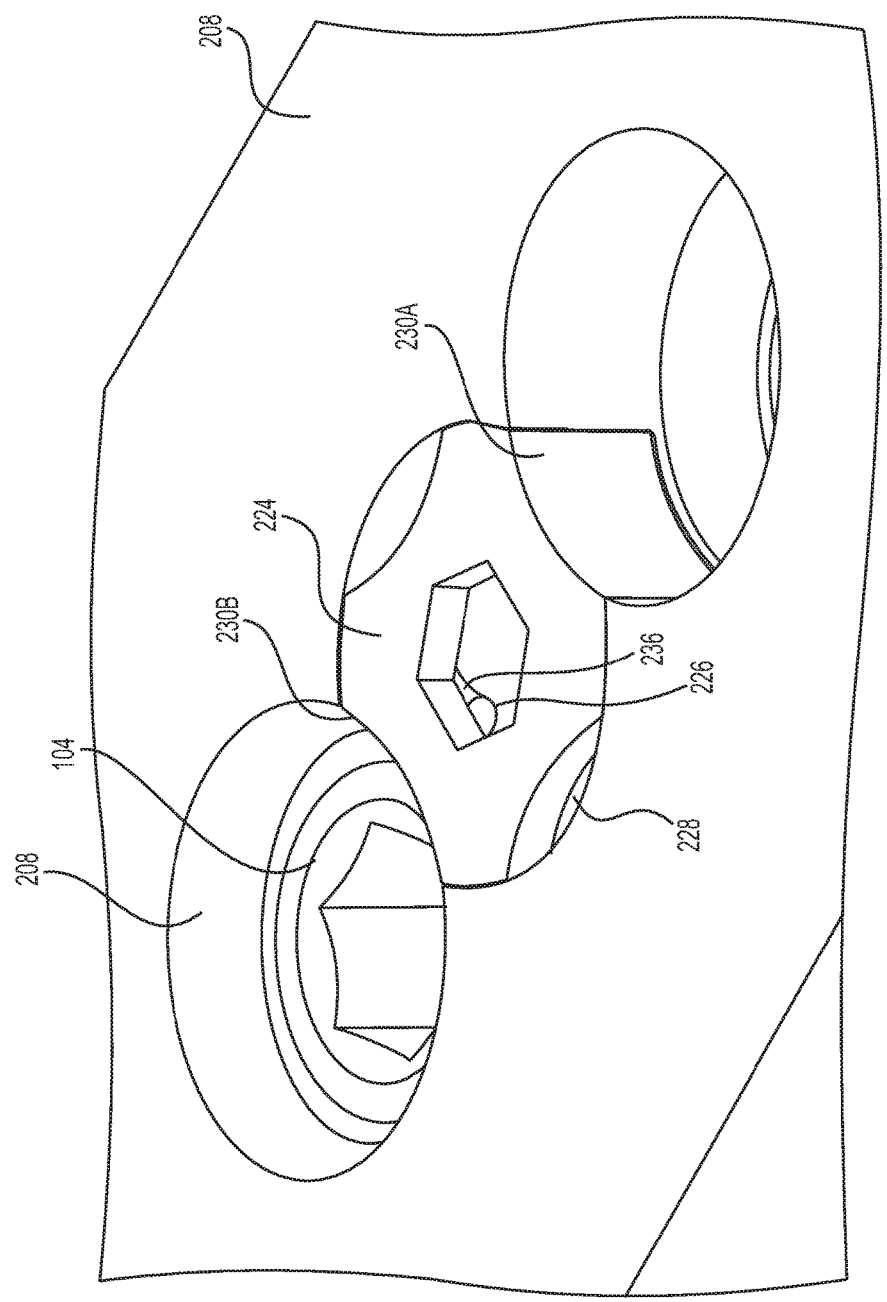
FIG. 9 is a perspective view of the spinal plate assembly of FIG. 8, wherein the locking mechanism is shown in an "unlocked" condition according to an alternate embodiment of the present invention.

FIG. 8 depicts a spinal plate assembly 200 having an integrated locking mechanism shown in a "locked" condition according to an alternate embodiment of the present invention. FIG. 9 depicts a spinal plate assembly 200 with integrated locking mechanism shown in an "unlocked" condition according to an alternate embodiment of the present invention. The spinal plate assembly 200 shown in these figures comprises: base plate 202, bone screw 104, locking mechanism 206, and aperture 208. The base plate 202 of the illustrative embodiment is preferably constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the elements of base plate 202 are made from a durable thermoplastic polymer, such as polyether ether ketone (PEEK).

It should be noted at this point of the disclosure that the locking mechanism of the present assembly 200 is adapted for use with plates and devices extending the spine and thoracic and lumbar regions, including but not limited to, cervical plates, thoracolumbar anterior and lateral plates.

In accordance with the illustrative embodiment, base plate 202 is an elongated structure having a lower surface 210 adapted to be placed against a plurality of vertebrae (not illustrated) and an opposite upper surface 212. In order to couple base plate 202 to vertebrae, base plate 202 has one or more apertures 208 therethrough for receiving one or more bone engaging fasteners, preferably bone screws 104. Bone screws 104 are implanted through apertures 208 to fix base plate 202 to adjacent vertebrae or bony element. Elongated threaded shank portion 114 of bone screws 104, shown in FIG. 21, extends downwardly from enlarged head portion 116 to fit inside aperture 208. Preferably, shape of outside of head portion 116 of each bone screw 104 substantially corresponds to the shape of aperture 208, although this is not a requirement.

Base plate 202 includes at least one locking mechanisms 206 moveable between "locked" and "unlocked" conditions. In the "locked" condition, as shown in FIG. 8, bone screw head 116 is prevented from backing out of aperture 208. In the "unlocked" condition, shown in FIG. 9, bone screw 104 is permitted to be removed from aperture 208.

Figure 10:
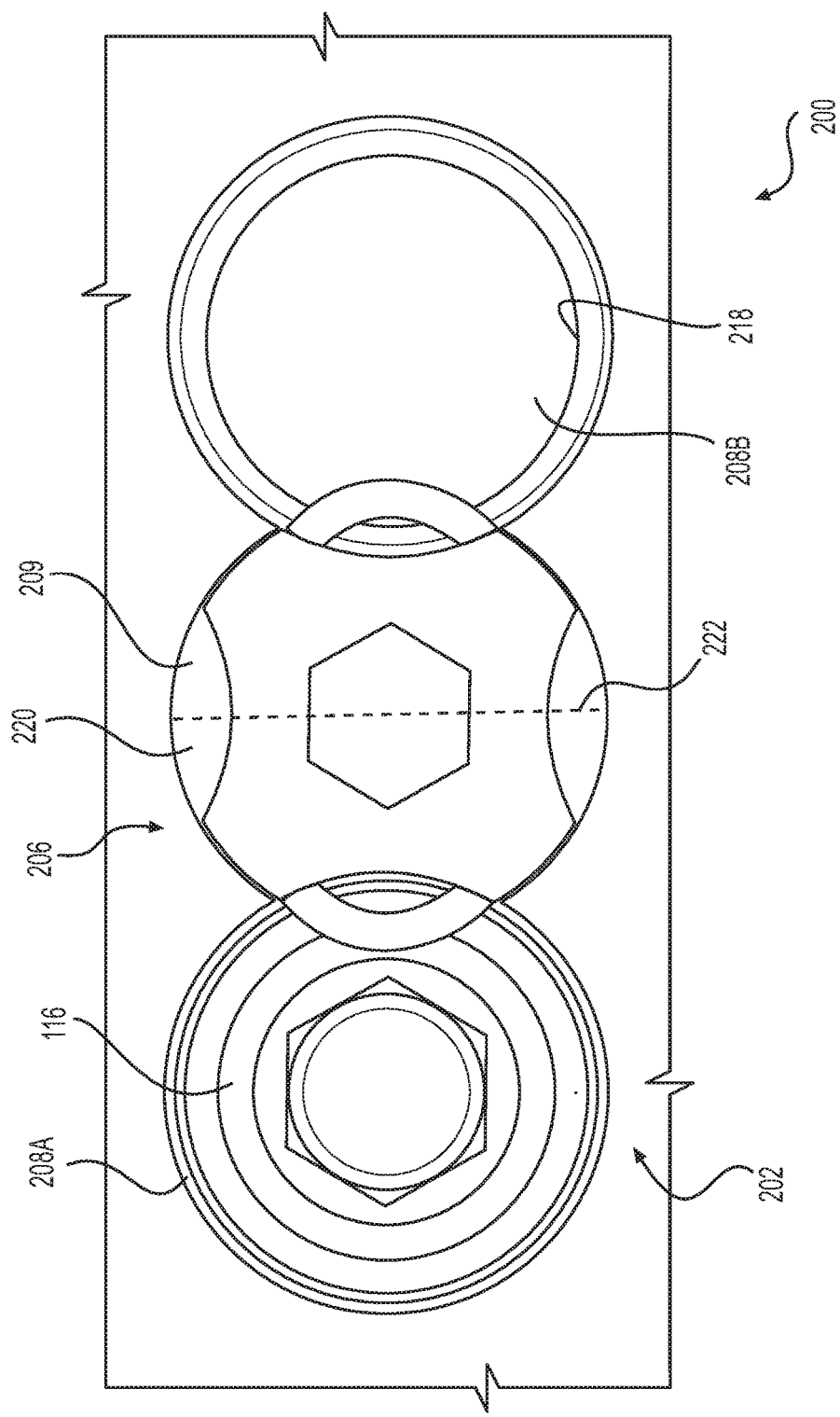
FIG. 10 is a top view of the spinal plate assembly of FIG. 8, depicting the elements that form the locking assembly in accordance with an alternate embodiment of the present invention.

FIG. 10 is a top view of spinal plate assembly 200 and elements that form locking mechanism 206. Arranged within base plate 202 are apertures 208, each of which is sized and shaped to accommodate bone screw 104. Each aperture 208 includes a seat 218. Specifically, the figure shows a first apertures 208A sized and shaped to receive first screw 104A, while a second aperture 208B is sized and shaped to receive second screw 104B (not shown). Base plate 202 includes at least one substantially circular opening 209 adjacent aperture 208 for receiving at least a portion of locking mechanism 206. Preferably, opening 209 is defined between two aligned apertures 208, and includes a contact wall 220 and a diameter 222. It should be noted at this point of the disclosure that one or more apertures 208 is contemplated. In the case of one aperture (not sure) locking mechanism 208 controls one bone screw 104. In the case of three apertures (not shown) locking mechanism 208 controls three bone screws 104 disposed in three separate apertures 208 simultaneously. Apertures 208 are shown in more detail in the following figures, which will now be discussed. It should also be noted at this point of the disclosure that first aperture 208A and second aperture 208B are substantially similar, albeit rotated around the central axis thereof from one other, and that same reference numerals have been used to indicate same parts or elements throughout the various figures and specification. For the purpose of clarity, the following discussion will use the generic word "aperture 208," to refer to both first and second apertures 208A, 208B.

Figure 11:
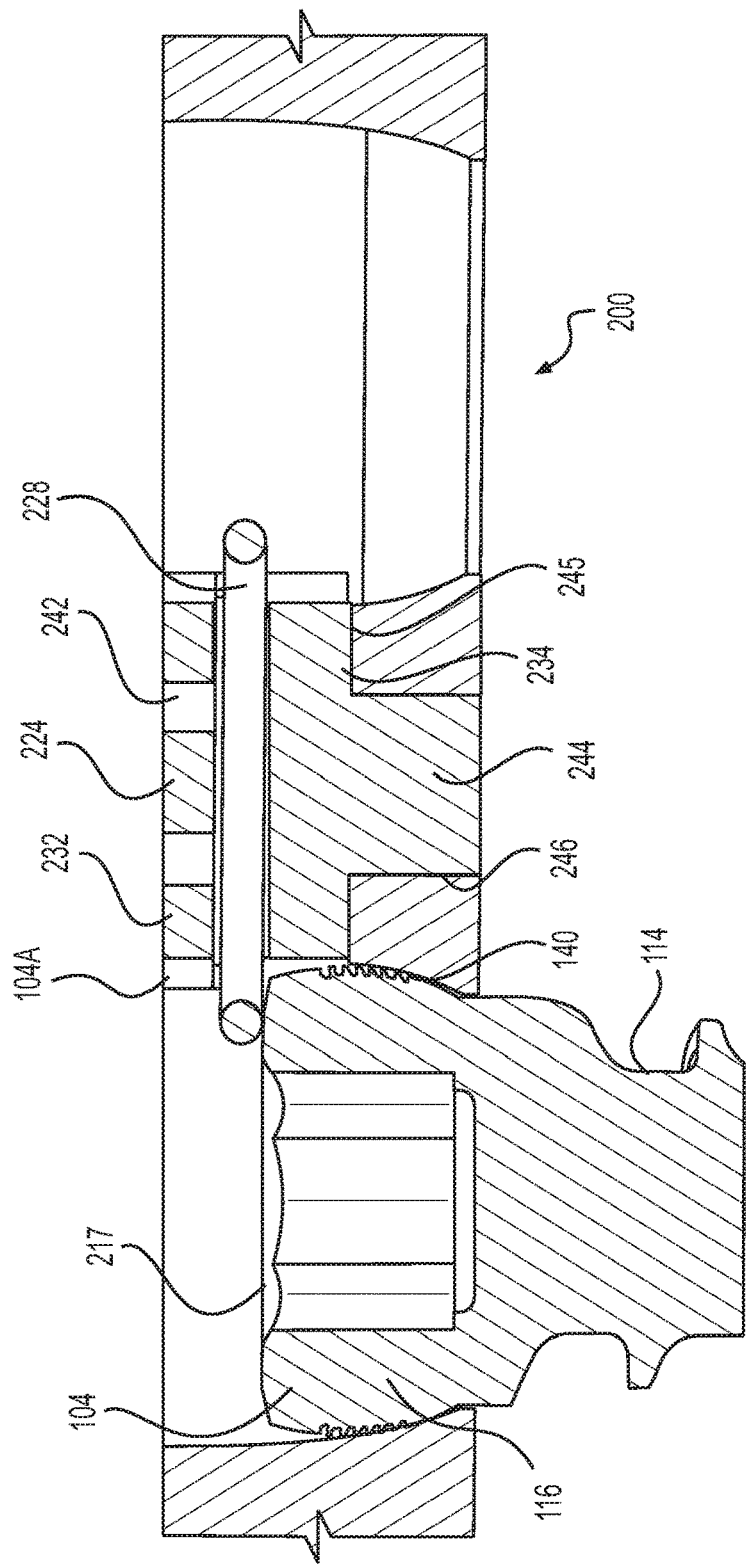
FIG. 11 is a side cross-sectional view of the spinal plate assembly of FIG. 8 in a "locked" condition in accordance with an alternate embodiment of the present invention.

FIG. 11 is a cross-section view of the spinal plate assembly of FIG. 8 in the "locked" condition. Locking mechanism 206 comprises moveable member 224, preferably a rotating member mounted within circular opening 209 between pair of apertures 208, and flexible element 226. Circular opening 209 has a seat 245 and a bore 246 extending axially therethrough for receiving rotating member 224. Rotating member 224 includes a head 240 having a pin 244 extending downwardly therefrom. Head 240 is received within opening 209 of base plate 202 adjacent seat 245, such that pin 244 is received within bore 246. Pin 244 passes all or partially through base plate 202 to couple rotating member 224 to base plate 202. Rotating member 224 rotates within opening about pin 244. Pin 244 may also include a threaded shaft (not shown) for securing the rotating member 224 within the opening 209. Head 240 of rotating member 224 is mounted flush with upper surface 212 of base plate 202 so as to not intrude upon the body or working area of the base plate. Head 240 may also protrude (not shown) from the base plate 202 as desired.

Head 240 of rotating member 224 includes an engaging portion 242 for receiving a driver. Preferably, the engaging portion 242 is a recess formed within head 240. Recess 242 allows a driving means, preferably a tool with a matching shaft (not shown), to rotate member 224 clockwise about pin 244 within opening 209. Tool as described in the illustrative embodiment has a hexagonal shaft for mating with a hexagonal recess 242 of head 240, but any other matching slotted, flat, triangle, square, star, rectangular, pentagonal, octagon, n-lobular, hexalobular, stardrive, Torx®, trilobular or other keyed shape is possible.

Figure 12:
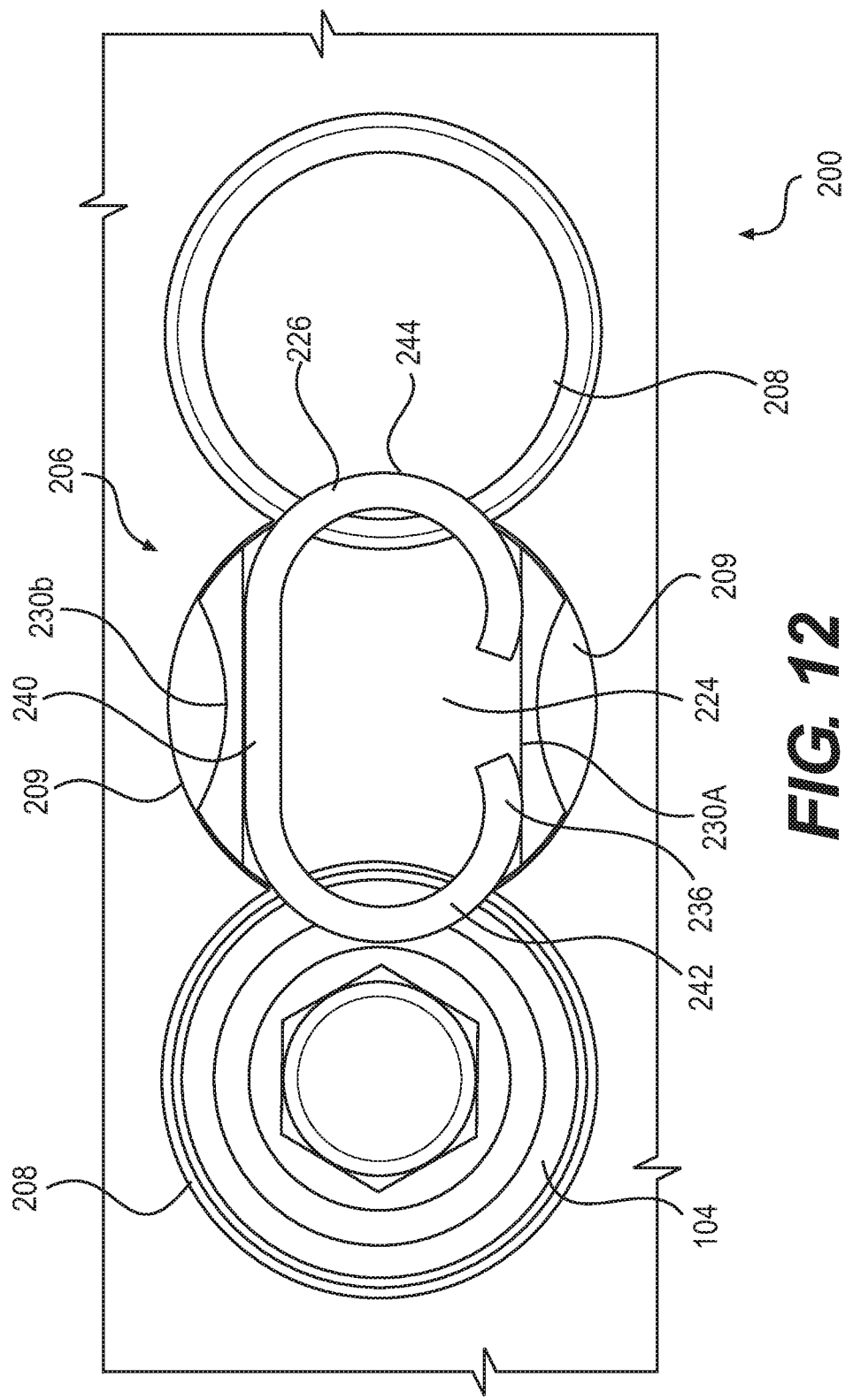
FIG. 12 is a top cross-sectional view of the spinal plate assembly of FIG. 8 in a "locked" condition in accordance with an alternate embodiment of the present invention.

FIG. 12 is a cross-section view of the spinal plate assembly of FIG. 8 in the "locked" condition in accordance with an alternate embodiment of the present invention. Head 240 of rotating member 224 includes a top surface 232 and a bottom surface 234 and a groove 228 extending circumferentially therearound midway between top and bottom surface 234. Head 240 includes oppositely positioned wedging walls 230A, 230B adjacent circumferential groove 228, which are sized and shaped to compress flexible element 226 between "locked" and "unlocked" conditions.

Flexible element 226 is preferably a deformable split ring 226 having a first end 236, a second end 238, and a midpoint 240 substantially between first and second ends. Spilt ring 226 includes a first portion 242 between first end 236 and midpoint 240, and a second portion 244 between second end 238 and midpoint 240. First and second ends 236, 238 of split ring 226 are positioned within circumferential groove 228 adjacent curved wall 230A, and midpoint 240 is positioned within circumferential groove 228 adjacent oppositely curved wall 230B, such that ends and midpoint of split ring are compressed together between opposite wedging walls in the rotating member 224, thereby squeezing the split ring 226 to deform into the apertures 208. Specifically, first and second portions 242, 244 are deformed outwardly from circumferential groove 228 into apertures 208 in order to block screw heads 116 from backing out of apertures 208. When bone screw 104 includes shoulder recess 104B, shown in FIG. 22, flexible element 226 rests adjacent shoulder recess 104b, which reduces overall height of plate 202.

First and second portions 242, 244 of split ring 226 are compressed inwardly into circumferential groove 228 of rotating member 224 as bone screws 104 are inserted into apertures 208, thereby allowing bone screw heads 116 to pass through and be seated in apertures 208. Once screws 104 are seated within apertures 208, first and second portions 242, 244 of split rings 226 return to "locked" condition partially blocking apertures 208 for retaining bone screw 104.

Figure 13:
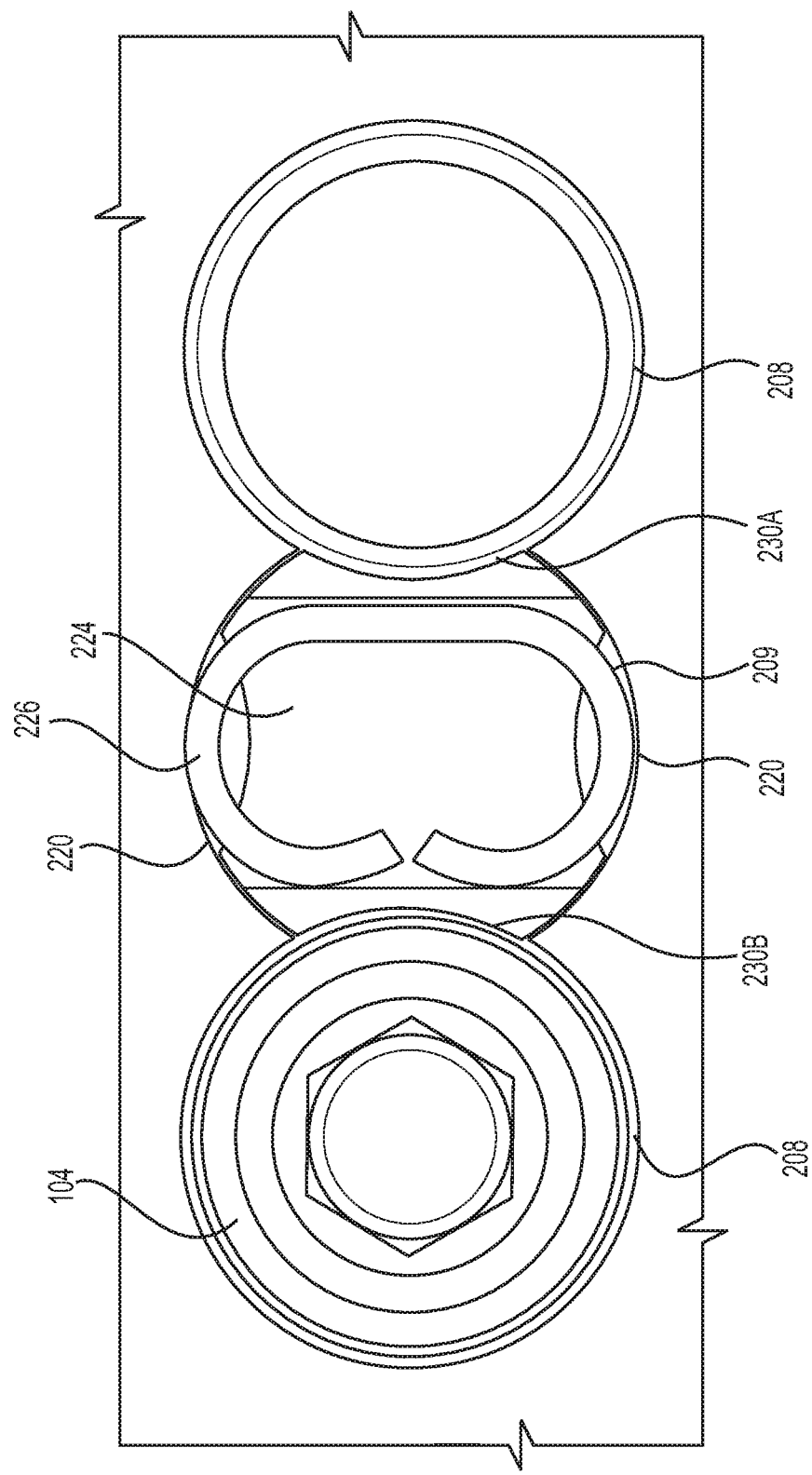
FIG. 13 is a top cross-sectional view of the spinal plate assembly of FIG. 9 in an "unlocked" condition in accordance with an alternate embodiment of the present invention.
Figure 14:
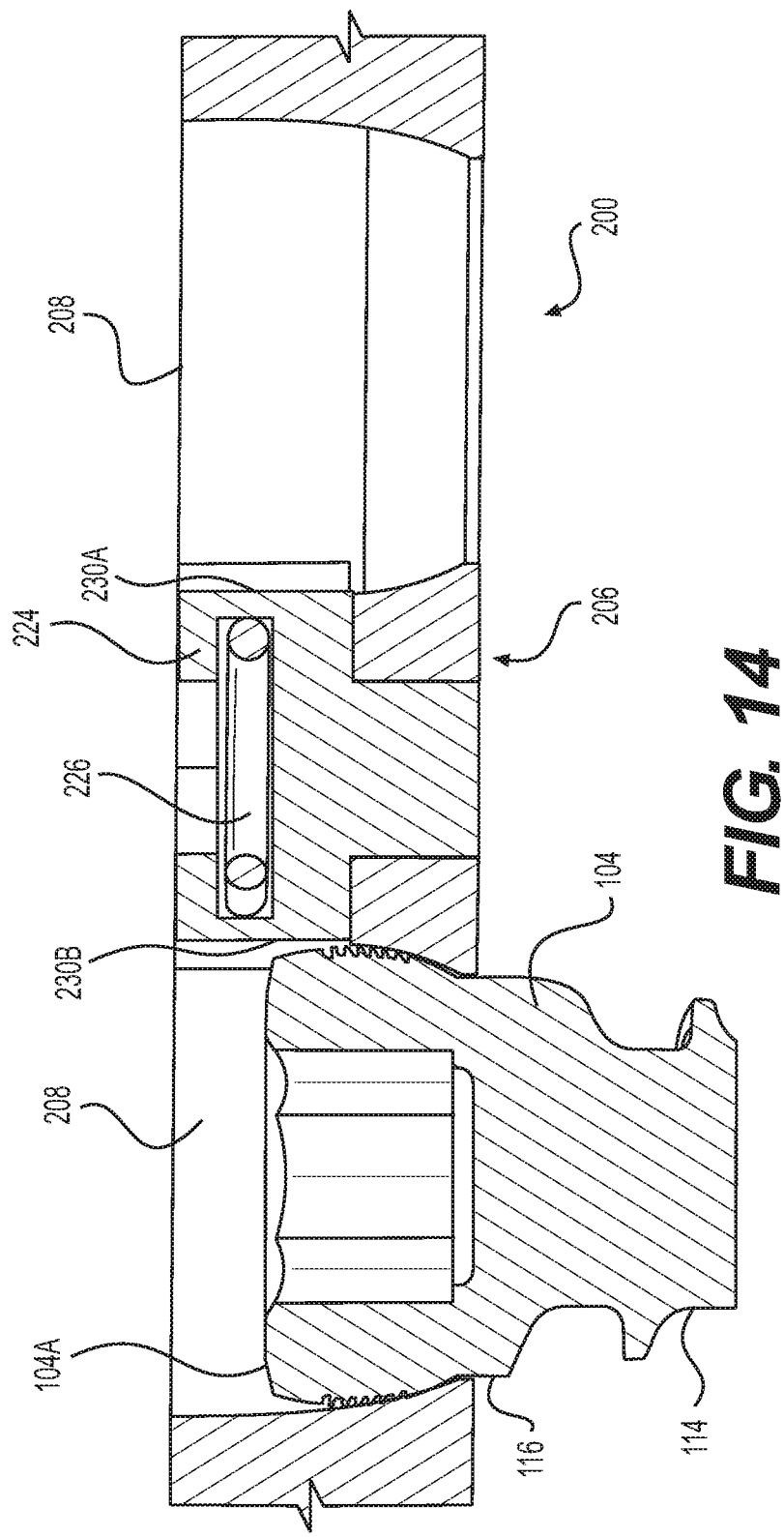
FIG. 14 is a side cross-sectional view of the spinal plate assembly of FIG. 9 in an "unlocked" condition in accordance with an alternate embodiment of the present invention.

FIGS. 13 and 14 are cross-sectional views of the spinal plate assembly of FIG. 9 in an "unlocked" condition in accordance with an alternate embodiment of the present invention. To achieve "unlocked" condition, rotating member 224 is rotated a quarter turn clockwise or counterclockwise within opening 209, such that opposite wedging walls 230A, 230B align with respective apertures 208 to block split ring 226 from extending into apertures 208. In this position, first and second portions 242, 244 of split ring 226 are retained between contact wall 220 of opening 209, while ends 236, 238 and midpoint 240 of split ring are compressed between wedging walls 230A, 230B. Using driving tool (not shown), bone screws are then removed from apertures 208.

Loaded Rotating Member

Figure 15A:
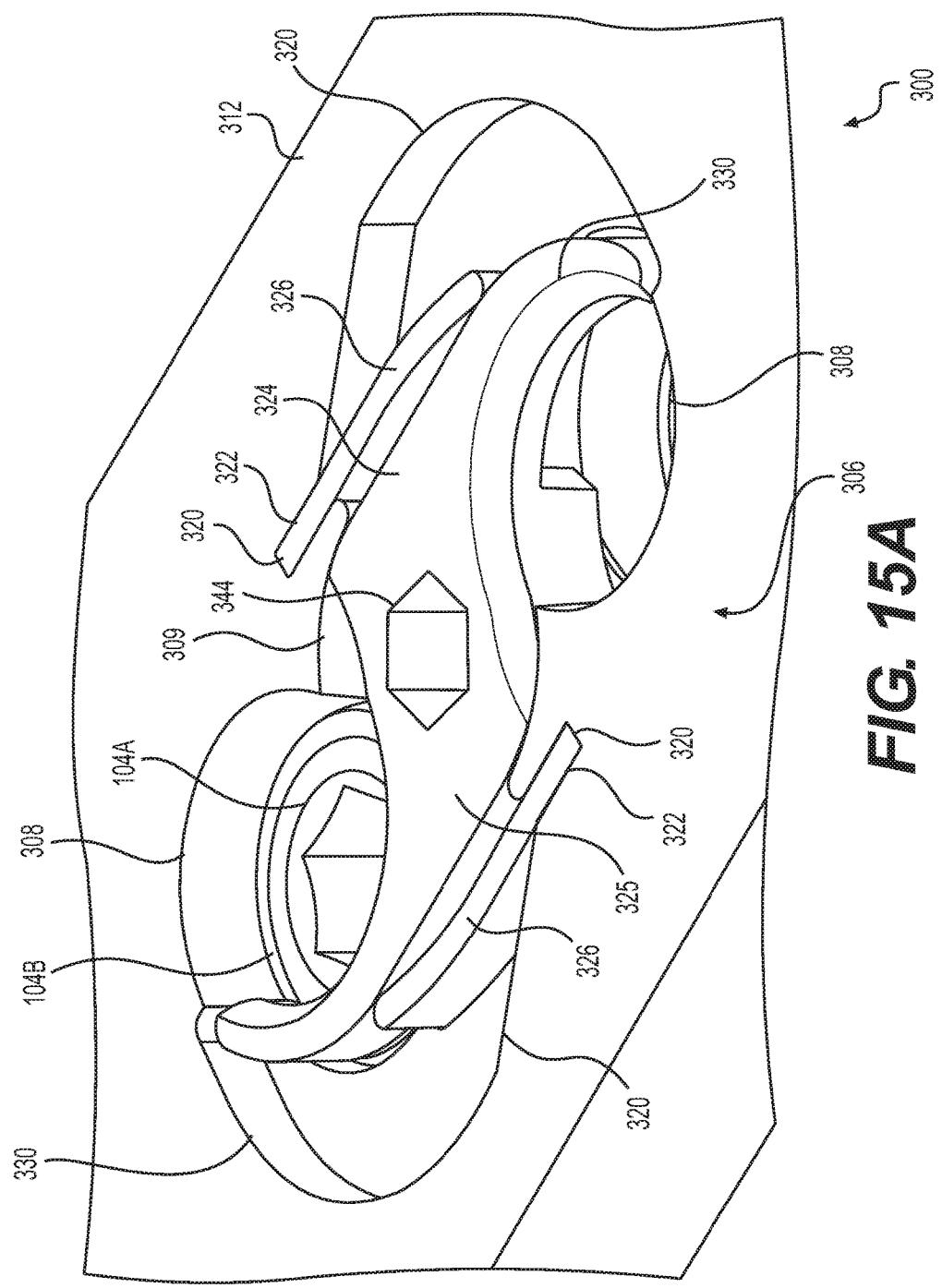
FIG. 15A is a perspective view of a spinal plate assembly having an integrated locking mechanism shown in a "locked" condition according to yet another alternate embodiment of the present invention.
Figure 15C:
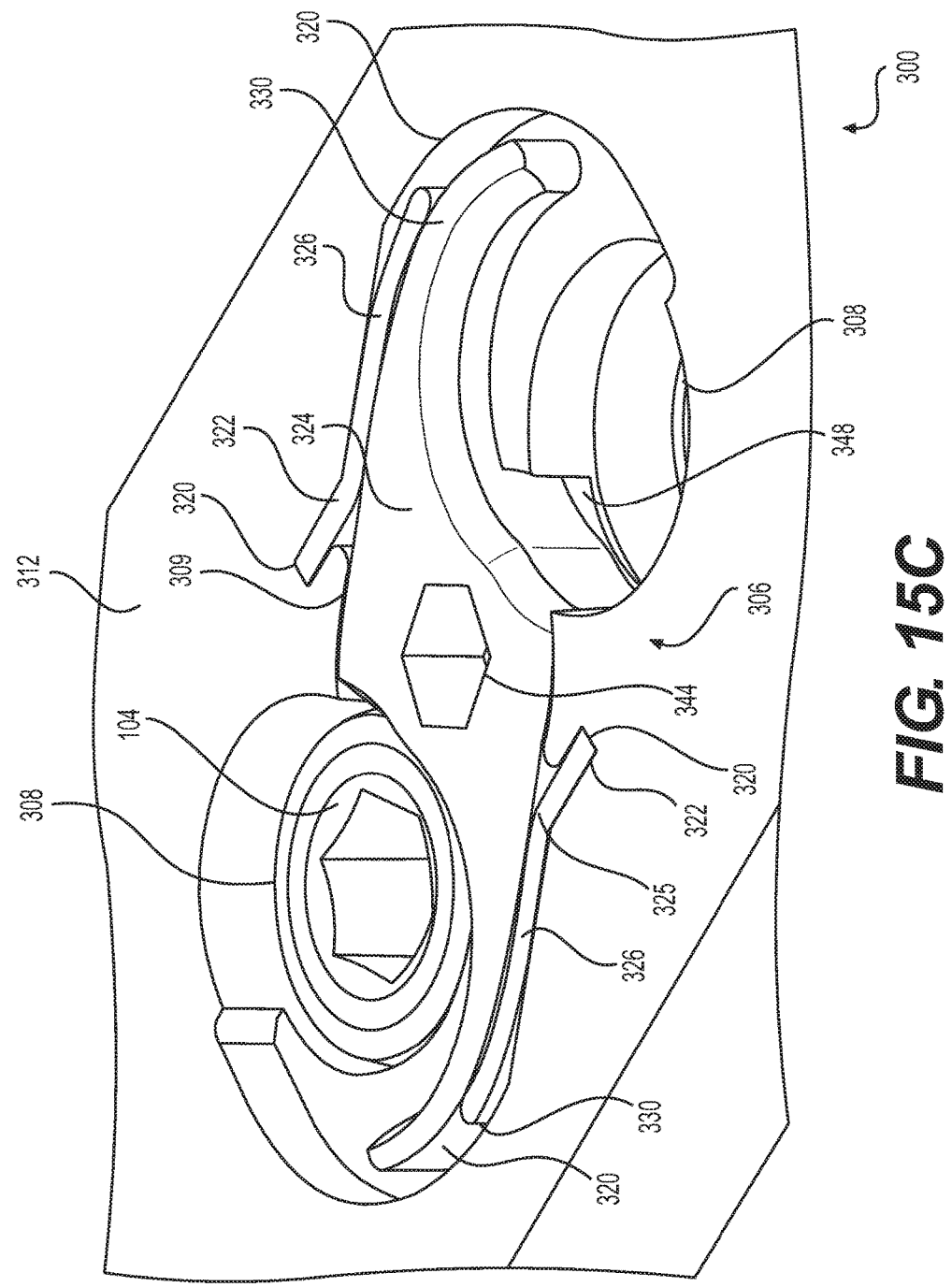
FIG. 15C is a perspective view of a spinal plate assembly having an integrated locking mechanism including shown in an "unlocked" condition according to an alternate embodiment of the present invention.

FIG. 15A depicts a spinal plate assembly 300 having integrated locking mechanism shown in a "locked" condition according to an alternate embodiment of the present invention. FIG. 15B depicts spinal plate assembly 300 having integrated locking mechanism shown in an "as inserted" condition according to an alternate embodiment of the present invention. FIG. 15C depicts spinal plate assembly 300 having integrated locking mechanism shown in an "unlocked" condition according to an alternate embodiment of the present invention. The spinal plate assembly 300 shown in these figures comprises: base plate 302, bone screw 104, locking mechanism 306, and aperture 308. The base plate 302 of the illustrative embodiment is preferably constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the base plate 302 are made from a durable thermoplastic polymer, such as polyether ether ketone (PEEK).

It should be noted at this point of the disclosure that the locking mechanism of the present assembly 300 is adapted for use with plates and devices extending the spine and thoracic and lumbar regions, including but not limited to, cervical plates, thoracolumbar anterior and lateral plates.

In accordance with the illustrative embodiment, base plate 302 is an elongated structure having a lower surface 310 adapted to be placed against a plurality of vertebrae (not illustrated) and an opposite upper surface 312. In order to couple base plate 302 to vertebrae, base plate 302 has one or more apertures 308 therethrough for receiving one or more bone engaging fasteners, preferably bone screws 104. Bone screws 104 are implanted through apertures 308 to fix base plate 302 to adjacent vertebrae or bony element. Elongated threaded shank portion 114 of bone screws 104, shown in FIG. 21, extend downwardly from enlarged head portion 116 to fit inside aperture 308. Preferably, shape of outside of head portion 116 of each bone screw 104 substantially corresponds to the shape of aperture 308, although this is not a requirement.

Base plate 302 includes at least one locking mechanisms 306 moveable between "locked" and "unlocked" conditions. In the "locked" condition, as shown in FIG. 15A, bone screw head 116 is prevented from backing out of aperture 308. In the "as inserted" condition, shown in FIG. 15B, bone screw 104 is permitted to be inserted into aperture 308. In the "unlocked" condition, shown in FIG. 15C, bone screw 104 is permitted to be removed from aperture 308.

Figure 16:
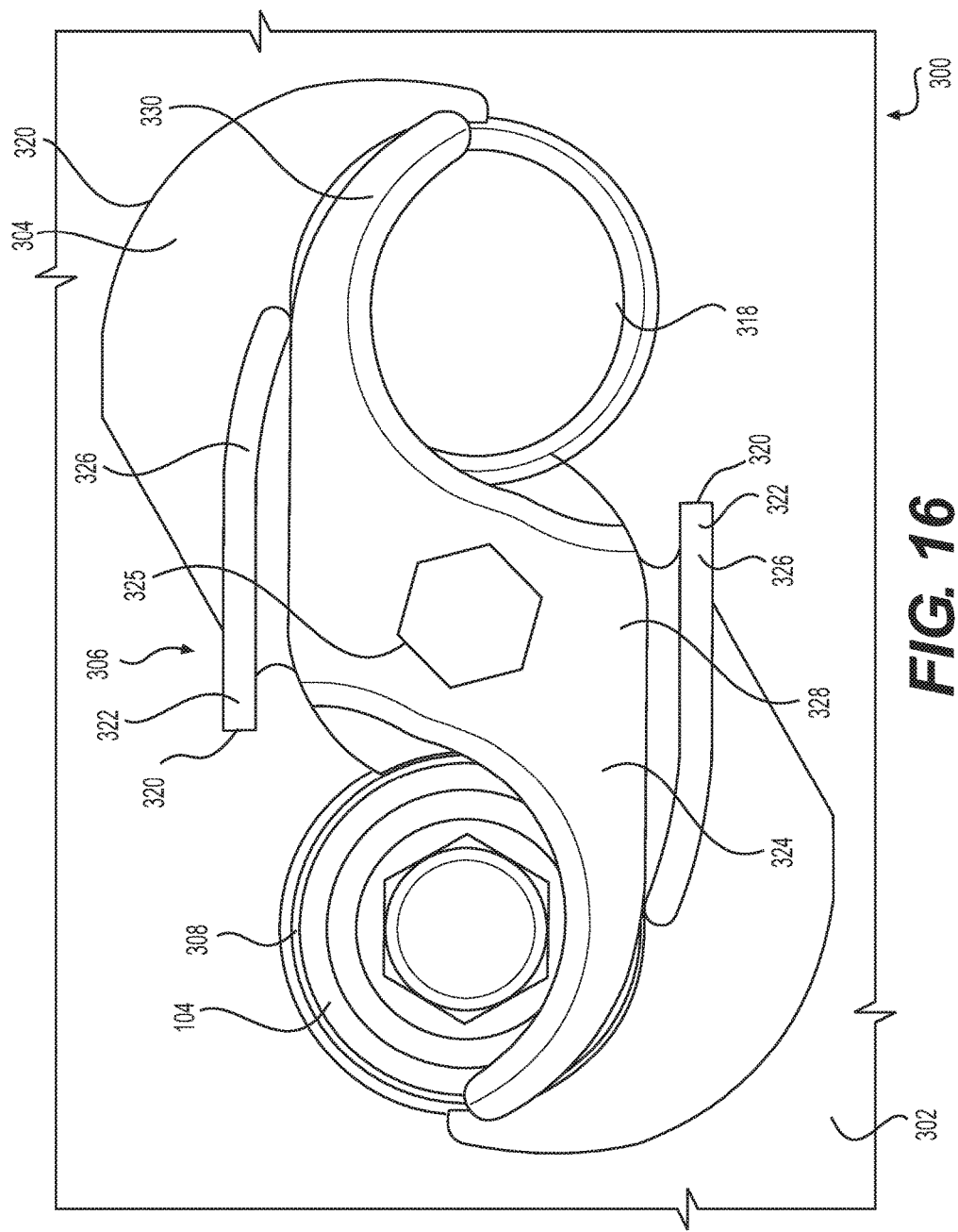
FIG. 16 is a top view of a spinal plate assembly of FIG. 15A, the assembly having an integrated locking mechanism including a screw shown in a "locked" condition according to an alternate embodiment of the present invention.
Figure 17:
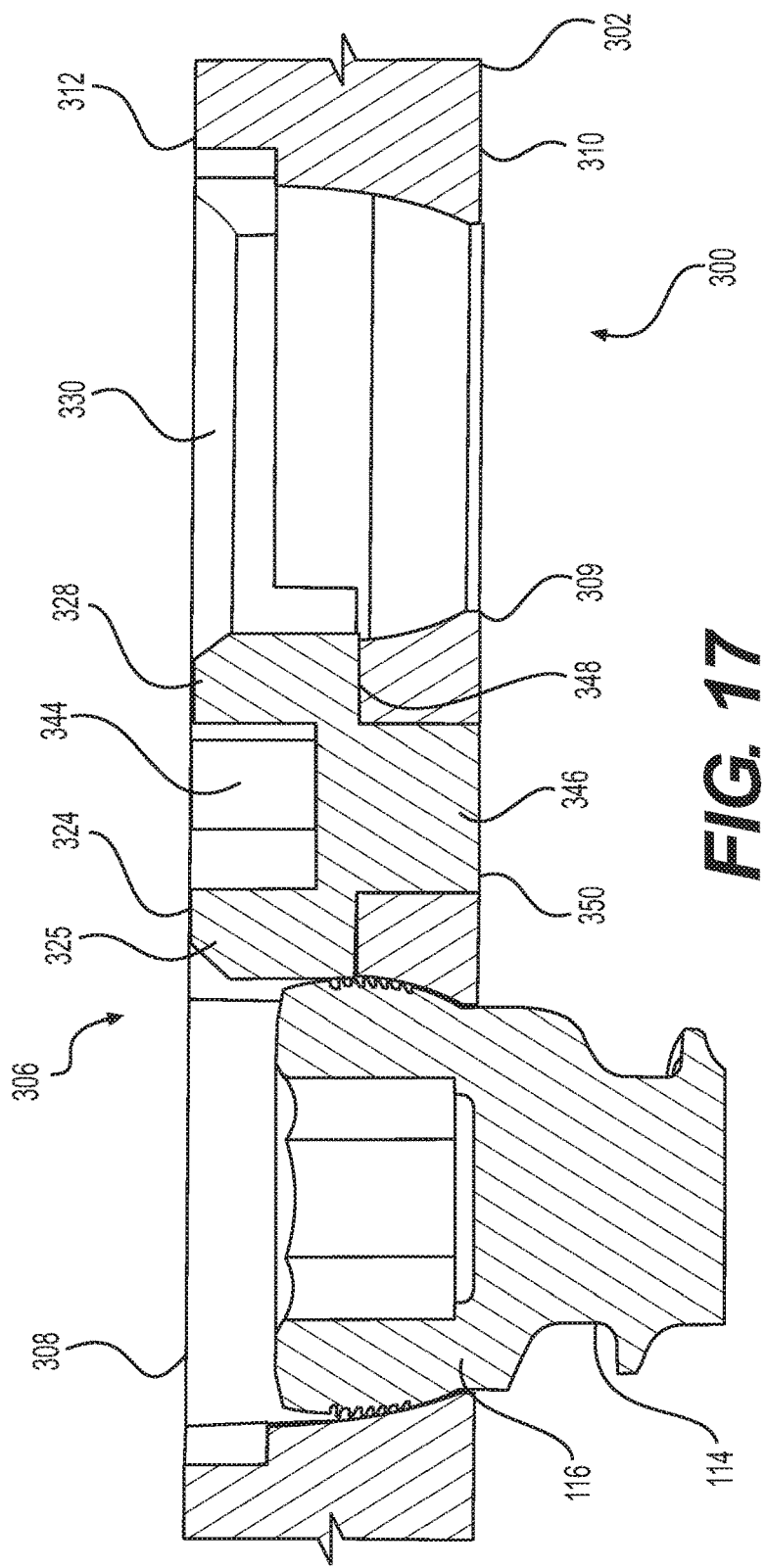
FIG. 17 is a cross-sectional view of the spinal plate assembly of FIG. 15A in a "locked" condition in accordance with an alternate embodiment of the present invention.
Figure 18:
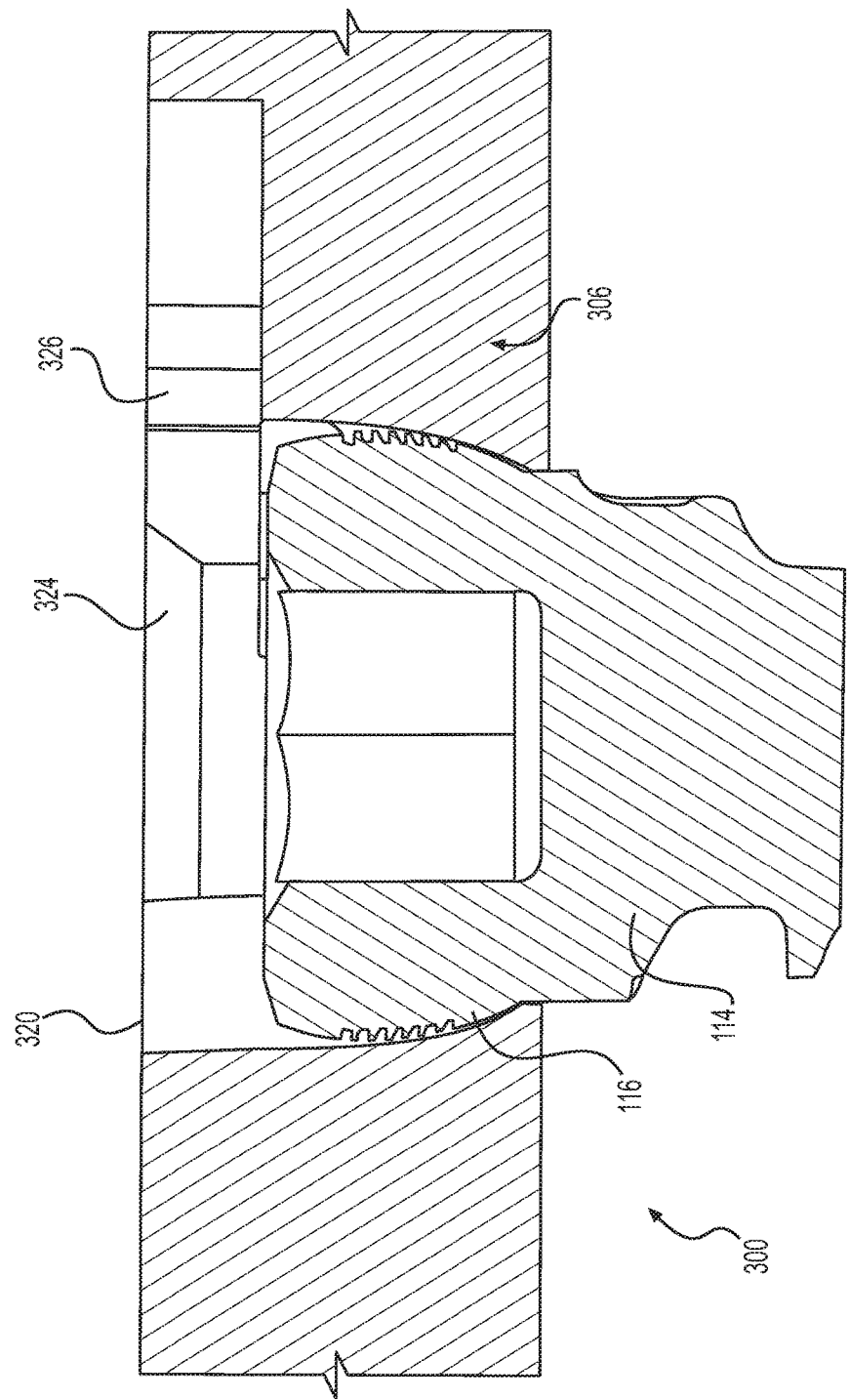
FIG. 18 is a cross-sectional side view of the spinal plate assembly of FIG. 15A in a "locked" condition in accordance with an alternate embodiment of the present invention.

FIGS. 16-18 illustrate spinal plate assembly 300 and elements that form the locking mechanism 306 in a "locked" condition according to an alternate embodiment of the present invention. In particular, FIG. 16 is a top view of spinal plate assembly 300, FIG. 17 is a cross-sectional view of the spinal plate assembly, and FIG. 18 is a side cross-sectional view of the spinal plate assembly. These figures illustrate two apertures 308 arranged within base plate 302, each of which is sized and shaped to accommodate bone screw 104. Each aperture 308 includes a seat 318 for receiving head portion 116 of bone screw 104 thereon. Specifically, apertures 308 include a first apertures 308A sized and shaped to receive first screw 104A, and a second aperture 308B is sized and shaped to receive second screw 104B (not shown). Base plate 302 includes at least one substantially S-shaped opening 309 extending between and partially around apertures 308A, 308B. Opening 309 has a seat 348 and a bore 350 extending axially therethrough. Opening 309 further includes a contact wall 320 and a pair of pockets 322 recessed within the contact wall 320.

Locking mechanism 306 comprises moveable member 324, preferably a rotating member mounted within opening 309, and one or more flexible elements 326. Rotating member 324 includes a substantially S-shaped main body 325 having a pin 346 extending downwardly therefrom 346. Main body 325 includes a flex section 328 and a pair of curved screw engaging sections 330 at opposite ends thereof. Main body 325 is received within opening 309 of base plate 302 adjacent seat 348, such that pin 346 is received within bore 348. Pin 346 passes all or partially through base plate 302 to couple rotating member 324 to base plate 302. Rotating member 324 rotates within opening 309 about pin 346. Pin 346 may also include a threaded shaft (not shown) for securing the rotating member 324 within the opening 309. Main body 325 of rotating member 324 is mounted flush with upper surface 312 of base plate 302 so as to not intrude upon the body or working area of the base plate. Main body 325 may also protrude (not shown) from the base plate 302 as desired.

Main body 325 of rotating member 324 includes an engaging portion 344 for receiving a driver 344. Preferably, the engaging portion 344 is a recess formed within flex section 328 of rotating member 324. Recess 344 allows a driving means, preferably a tool with a matching shaft (not shown), to pivotally rotate rotating member 324 counterclockwise about pin 346. Tool as described in the illustrative embodiment has a hexagonal shaft for mating with a hexagonal recess 344 of flex section 328, but any other matching slotted, flat, triangle, square, star, rectangular, pentagonal, octagon, n-lobular, hexalobular, stardrive, Torx®, trilobular or other keyed shape is possible.

Flexible elements 326 are a pair of loaded members 326 each partially retained within pockets 322 of opening 309 and moveable between a "locked" condition and an "unlocked" condition. Loaded members 326 are positioned within respective pockets 322 so as to apply constant force to screw engaging sections 330 of rotating member 324. In the "locked" condition, loaded members 326 extend outwardly from pockets 322 driving the rotating member toward apertures 308 and away from contact wall 320. In this condition, rotating member 324 is forced to rotate clockwise causing screw engaging sections 330 to at least partially cover apertures 308 to prevent bone screws 104 from backing out of apertures 308.

Figure 19:
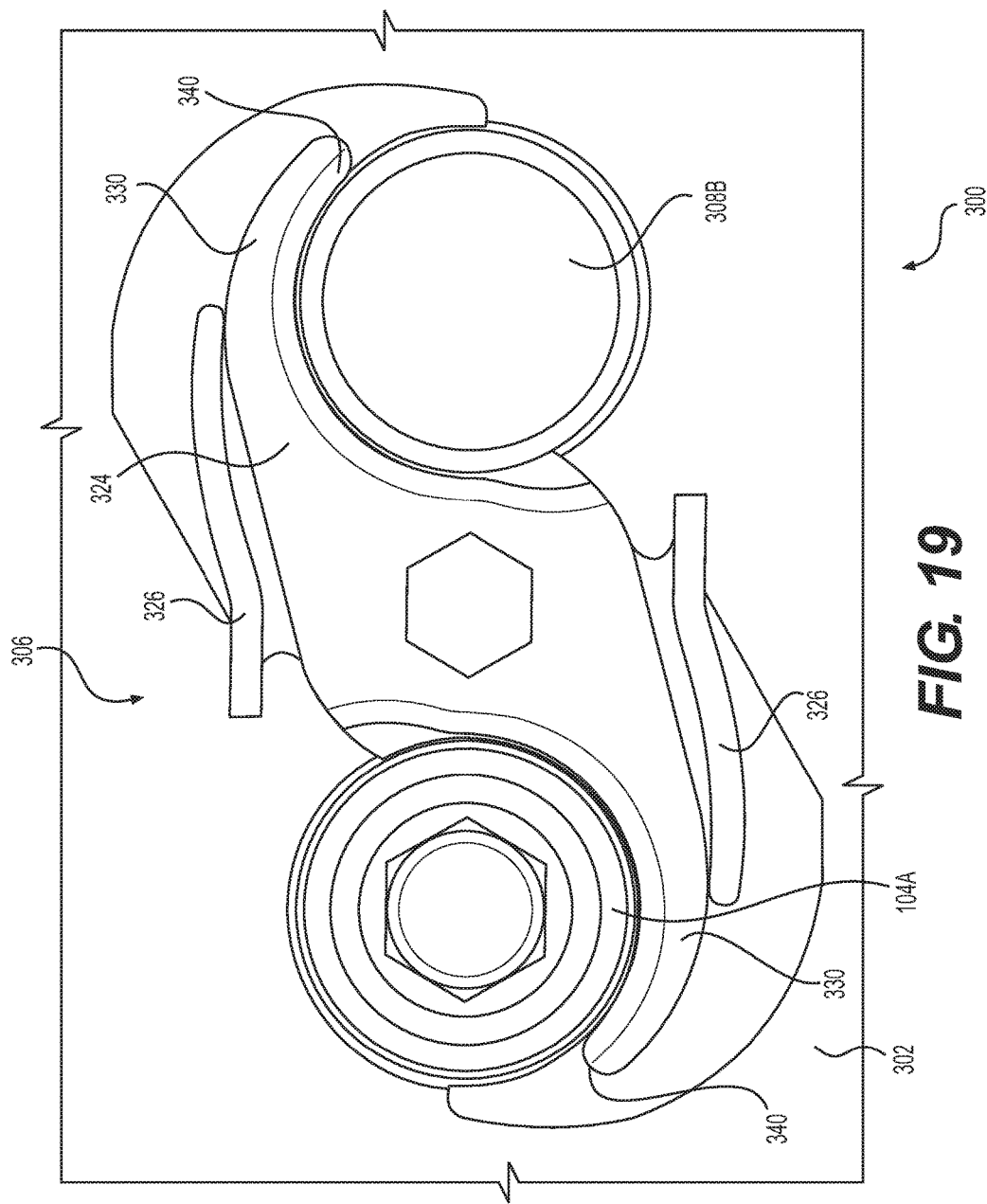
FIG. 19 is a top view of a spinal plate assembly having an integrated locking mechanism including a screw shown in an "as inserted" condition according to an alternate embodiment of the present invention.

FIG. 19 is a top view of the spinal plate assembly 300 and elements that form the locking mechanism 306 in an "as inserted" condition according to an alternate embodiment of the present invention. Each curved screw engaging sections 330 includes a leading edges 340, which engages with bone screw 104 and pushes rotating member 324 outwardly away from aperture 308 as bones screw 104 is inserted into aperture 308. In this condition, rotating member 324 is forced to rotate counterclockwise such that screw engaging portions 330 force loaded members 326 to compress within pockets 322 and deform toward contact wall 320 allowing bone screw 104 to be seated in aperture 308. When bone screw 104 includes shoulder recess 104B, shown in FIG. 22, screw engaging portion 330 rests adjacent shoulder recess 104b, which reduces overall height of plate 302.

Figure 20:
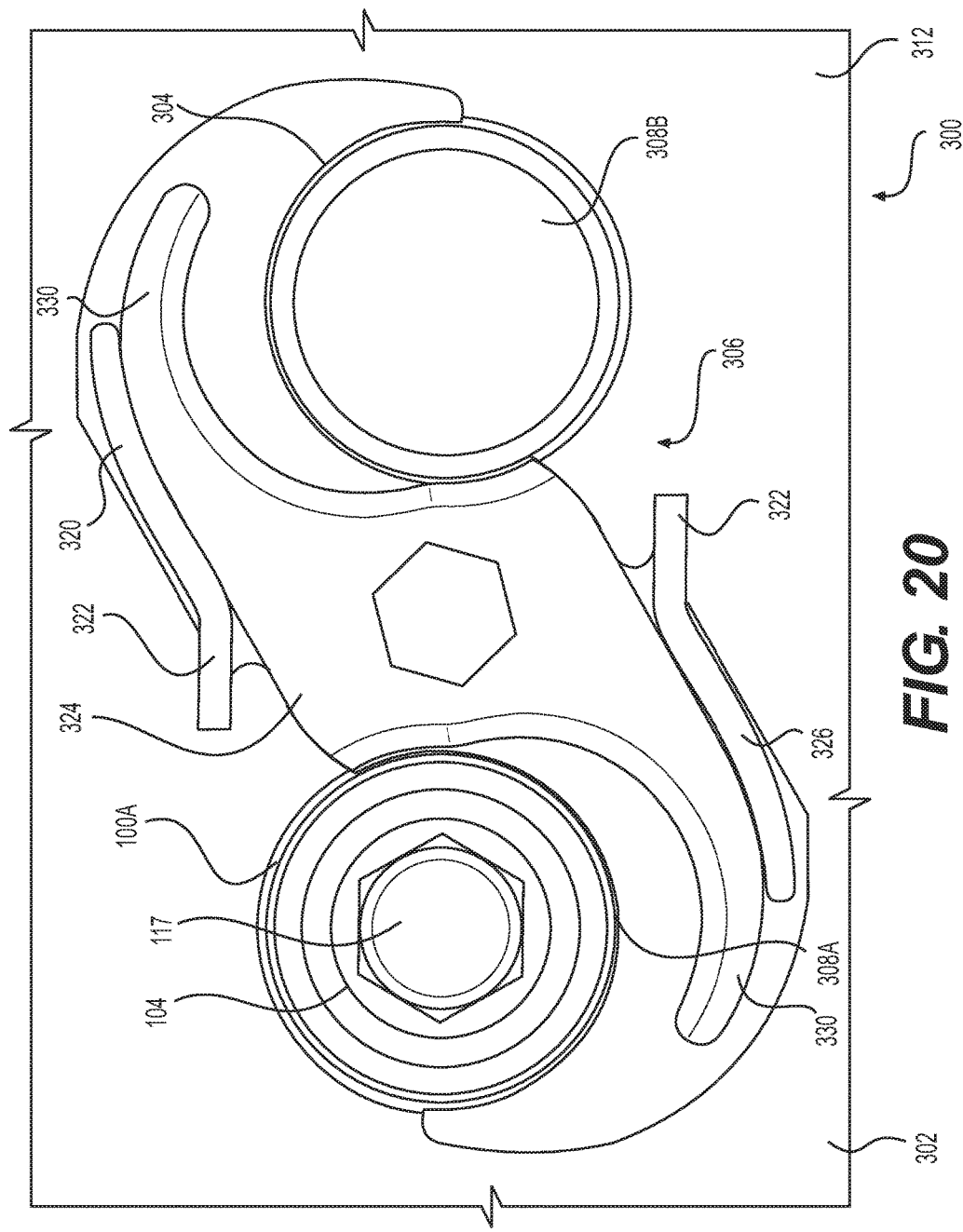
FIG. 20 is a top view of the spinal plate assembly having an integrated locking mechanism including shown in an "unlocked" condition according to an alternate embodiment of the present invention.

FIG. 20 is a top view of the spinal plate assembly 300 and elements that form the locking mechanism 306 in an "unlocked" condition according to an alternate embodiment of the present invention. In this position, rotating member 324 is further rotated, preferably by the driving means, toward a "capture point", which retains rotating member 324 in an "unlocked" condition. Using driving tool (not shown), bone screws 104 are then removed from apertures 308.

It is to be understood that the disclosure describes a few embodiments and that many variations of the invention can easily be devised by those skilled in the art after reading this disclosure and that the scope of the present invention is to be determined by the following claims.

What is claimed is:

1. A spinal plate assembly comprising:
   a base plate defining at least one aperture for receiving a screw, the at least one aperture including a seat and an annular groove terminating at an end wall;
   a flexible element having a distal end and a proximal end, the flexible element partially retained within the annular groove and moveable between a locked condition partially blocking the at least one aperture for retaining the screw in the seat and an unlocked condition radially deformable in the annular groove for permitting the screw to be removed from the at least one aperture;
   a moveable member for biasing the flexible element toward the unlocked condition, wherein the proximal end of the flexible element is configured to contact the moveable member and the distal end of the flexible element is configured to contact the end wall, and
   wherein in the locked condition the flexible element rests adjacent a top of the screw and substantially surrounds a head of the screw.

2. The spinal plate assembly of claim 1, wherein the flexible element is a resiliently deformable split ring.

3. The spinal plate assembly of claim 1, further comprising a bone screw sized to be inserted through the at least one aperture such that the bone screw sits within the seat of the at least one aperture for engaging a spinal vertebra, wherein the bone screw further comprises a top, wherein the flexible element blocks the at least one aperture in the locked condition by engaging the top of the bone screw.

4. The spinal plate assembly of claim 3, wherein the top of the bone screw further comprises a circumferential recess for engaging the flexible element in the locked condition.

5. The spinal plate assembly of claim 4, wherein the annular groove is dimensioned to receive at least part of the flexible element, and wherein the end wall engages the distal end of the flexible element when the flexible element is in the unlocked condition.

6. The spinal plate assembly of claim 5, wherein the moveable member further comprises a notch configured to engage the proximal end of the flexible element such that rotation of the moveable member radially deforms the flexible element within the annular groove.

7. The spinal plate assembly of claim 1, wherein the base plate further comprises:
an opening adjacent the at least one aperture for retaining the moveable member, the opening configured to substantially correspond to a shape of the moveable member; and
a seat within the opening having a bore extending axially therethrough.

8. The spinal plate assembly of claim 7, wherein the moveable member further comprises:
a head having an engaging portion with a recess for receiving a driver; and
a pin extending from the head portion configured to be disposed within and retained by the bore of the seat.

9. The spinal plate assembly of claim 8, wherein the recess has a cross-section selected from the group consisting of: slotted, square, triangular, rectangular, pentagonal, hexagonal, octagonal, n-lobular, hexalobular, stardrive, and trilobular.

10. The spinal plate assembly of claim 7, wherein the opening is configured to retain the moveable member between a pair of apertures to simultaneously bias more than one flexible element toward the unlocked condition.

11. The spinal plate assembly of claim 1, wherein the base plate includes an upper surface such that the moveable member is configured to be positioned flush with or beneath the upper surface of the base plate.

12. A spinal plate assembly comprising:
a base plate defining an opening adjacent at least one aperture for receiving a bone screw which attaches to a spinal vertebra, the opening including a seat having a bore extending axially therethrough, the at least one aperture including an annular groove terminating at an end wall; and
a locking mechanism having a flexible element having a distal end and a proximal end, the flexible element partially retained within the annular groove and moveable between a locked condition and an unlocked condition, and a rotating member positioned within the opening of the base plate for rotating the flexible element toward the unlocked condition, wherein the rotating member includes a head having an engaging portion for receiving a driver, a pin extending from the head configured to be inserted within the bore of the seat, and wherein the proximal end of the flexible element is configured to contact the rotating member and the distal end of the flexible element configured to contact the end wall,
wherein the flexible element partially blocks the at least one aperture preventing the screw from backing out of the at least one aperture in the locked condition,
wherein the rotating member forces the flexible element to radially deform within the annular groove permitting the screw to be removed from the at least one aperture in the unlocked condition, and
wherein in the locked condition the flexible element rests adjacent a top of the screw and substantially surrounds a head of the screw.

13. The spinal plate assembly of claim 12, wherein the flexible element is a resiliently deformable split ring.

14. The spinal plate assembly of claim 13, wherein the annular groove is dimensioned to receive at least part of the flexible element, and wherein the end wall engages the distal end of the flexible element when the flexible element is in the unlocked condition.

15. The spinal plate assembly of claim 14, wherein the rotating member further comprises a notch configured to engage the proximal end of the flexible element such that rotation of the rotating member radially deforms the flexible element within the annular groove.

16. The spinal plate assembly of claim 15, wherein the engaging portion is a recess having a cross-section shaped to receive a driving tool having a corresponding drive shaft.

17. The spinal plate assembly of claim 16, wherein the cross-section of the recess is selected from the group consisting of: slotted, square, triangular, rectangular, pentagonal, hexagonal, octagonal, n-lobular, hexalobular, stardrive, and tribolular.

18. The spinal plate assembly of claim 12, wherein the opening is configured to retain the rotating member between a pair of apertures to simultaneously rotate more than one flexible element toward the unlocked condition.

19. The spinal plate assembly of claim 12, wherein the base plate includes an upper surface such that the rotating member is configured to be positioned flush with or beneath the upper surface of the base plate.

20. A spinal plate assembly comprising:
a base plate having a first aperture, a second aperture, and an opening defined between the first and second apertures for coupling adjacent spinal vertebrae, the opening including a first seat having a bore extending axially therethrough, the first and second apertures each including a second seat and annular groove having an end wall;
a bone screw sized to be inserted through each aperture such that the bone screw sits within the seat of the respective aperture for engaging the spinal vertebrae; and
a locking mechanism having:
a first split ring at least partially disposed within the annular groove of the first aperture, a second split ring at least partially disposed within the annular groove of the second aperture, the first and second split rings each having a proximal end and a distal end,
wherein the split rings are moveable between the locked condition partially blocking the apertures for retaining the bone screws in the respective aperture seat, and the unlocked condition radially deforming into the annular grooves for permitting the bone screws to be removed from the apertures, and
a rotating member retained within the opening of the base plate having first and second diametrically opposed notches configured to engage the proximal ends of the first and second split rings respectively to simultaneously drive the split rings toward the unlocked condition, wherein the proximal ends of the respective split rings are configured to each contact the rotating member and the distal ends of the respective split rings are configured to each contact the respective end walls,
wherein in the locked condition the split rings rest adjacent a top of the respective screws and substantially surround a head of the respective screws, and
wherein the rotating member includes a recess shaped to receive a driving tool.

* * * * *